US011696718B2

(12) United States Patent
Chakravarthy et al.

(10) Patent No.: US 11,696,718 B2
(45) Date of Patent: Jul. 11, 2023

(54) ARRHYTHMIA DETECTION WITH FEATURE DELINEATION AND MACHINE LEARNING

(71) Applicant: Medtronic, Inc., Minneapolis, MN (US)

(72) Inventors: Niranjan Chakravarthy, Singapore (SG); Siddharth Dani, Minneapolis, MN (US); Tarek D. Haddad, Minneapolis, MN (US); Donald R. Musgrove, Minneapolis, MN (US); Andrew Radtke, Minneapolis, MN (US); Eduardo N. Warman, Maple Grove, MN (US); Rodolphe Katra, Blaine, MN (US); Lindsay A. Pedalty, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 17/373,480

(22) Filed: Jul. 12, 2021

(65) Prior Publication Data

US 2021/0338134 A1 Nov. 4, 2021

Related U.S. Application Data

(63) Continuation of application No. 16/850,699, filed on Apr. 16, 2020.
(Continued)

(51) Int. Cl.
*A61B 5/349* (2021.01)
*G16H 10/60* (2018.01)
*A61B 5/316* (2021.01)

(52) U.S. Cl.
CPC .............. *A61B 5/349* (2021.01); *A61B 5/316* (2021.01); *G16H 10/60* (2018.01); *A61B 2560/0214* (2013.01)

(58) Field of Classification Search
CPC .......... A61B 2560/0214; A61B 5/0205; A61B 5/316; A61B 5/349; A61B 5/352;
(Continued)

(56) References Cited

U.S. PATENT DOCUMENTS

| 4,458,691 A | 7/1984 | Netravali |
| 6,212,428 B1 | 4/2001 | Hsu et al. |

(Continued)

FOREIGN PATENT DOCUMENTS

| CN | 108030488 A | 5/2018 |
| EP | 1218060 B1 | 7/2002 |

(Continued)

OTHER PUBLICATIONS

International Preliminary Report on Patentability from International Application No. PCT/US2020/028707, dated Nov. 18, 2021, 8 pp.
(Continued)

*Primary Examiner* — George Manuel
(74) *Attorney, Agent, or Firm* — Shumaker & Sieffert, P.A.

(57) ABSTRACT

Techniques are disclosed for using both feature delineation and machine learning to detect cardiac arrhythmia. A computing device receives cardiac electrogram data of a patient sensed by a medical device. The computing device obtains, via feature-based delineation of the cardiac electrogram data, a first classification of arrhythmia in the patient. The computing device applies a machine learning model to the received cardiac electrogram data to obtain a second classification of arrhythmia in the patient. As one example, the computing device uses the first and second classifications to
(Continued)

determine whether an episode of arrhythmia has occurred in the patient. As another example, the computing device uses the second classification to verify the first classification of arrhythmia in the patient. The computing device outputs a report indicating that the episode of arrhythmia has occurred and one or more cardiac features that coincide with the episode of arrhythmia.

30 Claims, 10 Drawing Sheets

Related U.S. Application Data

(60) Provisional application No. 62/843,738, filed on May 6, 2019.

(58) Field of Classification Search
CPC ....... A61B 5/361; A61B 5/363; A61B 5/4839; A61B 5/686; A61B 5/7221; A61B 5/7267; A61B 5/742; A61N 1/3621; A61N 1/36507; A61N 1/36592; A61N 1/3756; G16H 10/60; G16H 15/00; G16H 40/63; G16H 40/67; G16H 50/20
See application file for complete search history.

(56) References Cited

U.S. PATENT DOCUMENTS

| | | |
|---|---|---|
| 6,308,094 B1 | 10/2001 | Shusterman et al. |
| 6,594,523 B1 | 7/2003 | Levine |
| 8,103,346 B2 | 1/2012 | Mass et al. |
| 8,521,281 B2 | 8/2013 | Patel et al. |
| 9,183,351 B2 | 11/2015 | Shusterman |
| 9,483,529 B1 | 11/2016 | Pasoi et al. |
| 9,585,590 B2 | 3/2017 | McNair |
| 9,743,890 B2 | 8/2017 | Lord et al. |
| 9,775,559 B2 | 10/2017 | Zhang et al. |
| 10,463,269 B2 | 11/2019 | Boleyn et al. |
| 10,744,334 B2 | 8/2020 | Perschbacher et al. |
| 11,355,244 B2 | 6/2022 | Haddad et al. |
| 2002/0016550 A1 | 2/2002 | Sweeney et al. |
| 2002/0123768 A1 | 9/2002 | Gilkerson et al. |
| 2006/0247709 A1 | 11/2006 | Gottesman et al. |
| 2009/0259269 A1 | 10/2009 | Brown |
| 2010/0179444 A1 | 7/2010 | O'Brien et al. |
| 2010/0268103 A1 | 10/2010 | McNamara et al. |
| 2010/0280841 A1 | 11/2010 | Dong et al. |
| 2011/0270109 A1 | 11/2011 | Zhang et al. |
| 2012/0004563 A1 | 1/2012 | Kim et al. |
| 2012/0209126 A1 | 8/2012 | Amos et al. |
| 2013/0274524 A1 | 10/2013 | Dakka et al. |
| 2013/0274624 A1 | 10/2013 | Mahanjan et al. |
| 2014/0257063 A1 | 9/2014 | Ong et al. |
| 2014/0378856 A1* | 12/2014 | Koike .................. A61B 5/7235 600/515 |
| 2015/0164349 A1 | 6/2015 | Gopalakrishnan et al. |
| 2015/0216435 A1 | 8/2015 | Bokan et al. |
| 2015/0265217 A1 | 9/2015 | Penders et al. |
| 2016/0022164 A1 | 1/2016 | Brockway et al. |
| 2016/0135706 A1 | 5/2016 | Sullivan et al. |
| 2016/0192853 A1 | 7/2016 | Bardy et al. |
| 2016/0220137 A1 | 8/2016 | Mahajan et al. |
| 2016/0232280 A1 | 8/2016 | Apte et al. |
| 2017/0095673 A1 | 4/2017 | Ludwig et al. |
| 2017/0105683 A1 | 4/2017 | Xue |
| 2017/0156592 A1 | 6/2017 | Fu |
| 2017/0196458 A1 | 7/2017 | Ternes et al. |
| 2017/0265765 A1 | 9/2017 | Baumann et al. |
| 2017/0290550 A1 | 10/2017 | Perschbacher et al. |
| 2017/0347894 A1* | 12/2017 | Bhushan .................. A61B 5/11 |
| 2017/0354365 A1 | 12/2017 | Zhou |
| 2018/0008976 A1 | 3/2018 | Okazaki |
| 2018/0089763 A1 | 3/2018 | Okazaki |
| 2018/0146874 A1 | 5/2018 | Walker et al. |
| 2018/0146929 A1 | 5/2018 | Joo et al. |
| 2018/0206721 A1 | 7/2018 | Zhang |
| 2018/0233227 A1 | 8/2018 | Galloway et al. |
| 2018/0272147 A1 | 9/2018 | Freeman et al. |
| 2018/0279891 A1 | 10/2018 | Miao et al. |
| 2018/0310892 A1 | 11/2018 | Perschbacher et al. |
| 2019/0008461 A1 | 1/2019 | Gupta et al. |
| 2019/0029552 A1 | 1/2019 | Perschbacher et al. |
| 2019/0038148 A1 | 2/2019 | Valys et al. |
| 2019/0038149 A1 | 2/2019 | Gopalakrishnan et al. |
| 2019/0090774 A1 | 3/2019 | Yang et al. |
| 2019/0122097 A1 | 4/2019 | Shibahara et al. |
| 2019/0209022 A1 | 7/2019 | Sobol et al. |
| 2019/0272920 A1 | 9/2019 | Teplitzky |
| 2019/0275335 A1 | 9/2019 | Volpe et al. |
| 2019/0328251 A1 | 10/2019 | Jin |
| 2019/0343415 A1 | 11/2019 | Saha et al. |
| 2019/0365342 A1 | 12/2019 | Ghaffarzadegan et al. |
| 2019/0378620 A1 | 12/2019 | Saren |
| 2020/0100693 A1 | 4/2020 | Velo |
| 2020/0108260 A1 | 4/2020 | Haddad et al. |
| 2020/0178825 A1 | 6/2020 | Weijia et al. |
| 2020/0288997 A1 | 9/2020 | Shute et al. |
| 2020/0352462 A1 | 11/2020 | Pedalty et al. |
| 2020/0352466 A1 | 11/2020 | Chakravarthy et al. |
| 2020/0352521 A1 | 11/2020 | Chakravarthy et al. |
| 2020/0353271 A1 | 11/2020 | Dani et al. |
| 2020/0357517 A1 | 11/2020 | Haddad et al. |
| 2020/0357518 A1 | 11/2020 | Musgrove et al. |
| 2020/0357519 A1 | 11/2020 | Chakravarthy et al. |
| 2021/0137384 A1 | 5/2021 | Robinson et al. |
| 2021/0169736 A1 | 6/2021 | Wijshoff et al. |
| 2021/0204858 A1 | 7/2021 | Attia et al. |
| 2021/0338134 A1 | 11/2021 | Chakravarthy et al. |
| 2021/0338138 A1 | 11/2021 | Pedalty et al. |
| 2021/0343416 A1 | 11/2021 | Chakravarthy et al. |
| 2021/0345865 A1 | 11/2021 | Spillinger et al. |

FOREIGN PATENT DOCUMENTS

| | | | |
|---|---|---|---|
| EP | 2427105 | A1 | 3/2012 |
| WO | 2010129447 | A1 | 11/2010 |
| WO | 2013/160538 | A1 | 10/2013 |
| WO | 2017072250 | A1 | 5/2017 |
| WO | 2017091736 | A1 | 6/2017 |
| WO | 2018119316 | A1 | 6/2018 |
| WO | 2020049267 | A1 | 3/2020 |

OTHER PUBLICATIONS

"Classify ECG Signals Using Long Short-Term Memory Networks," MATLAB, retrieved from https://www.mathworks.com/help/signal/examples/classify-ecg-signals-using-long-short-term-memory-networks.html, Nov. 2, 2018, 19 pp.

"Visualize Features of a Convolutional Neural Network," MATLAB & Simulink, Mar. 15, 2018, 9 pp.

Andersen et al., "A deep learning approach for real-time detection of atrial fibrillation," Expert Systems with Applications, ELSEVIER, available online Aug. 14, 2018, 9 pp.

Anonymous, "Receiver Operating Characteristic—Wikipedia," Mar. 20, 2019, Retrieved from the Internet: URL: https://en.wikipedia.org/w/index.php?title=Receiver_operating_characteristic&oldis=888671034#History, 12 pp.

International Search Report and Written Opinion of International Application No. PCT/US2020/028707, dated Aug. 10, 2020, 15 pp.

Kelwade et al., "Prediction of Cardiac Arrhythmia using Artificial Neural Network," International Journal of Computer Applications (0975-8887), vol. 115—No. 20, Apr. 2015, 6 pp.

Madani et al., "Fast and accurate view classification of echocardiograms using deep learning," NPJ Digital Medicine, vol. 1, No. 6 Mar. 21, 2018, 8 pp.

Schirrmeister et al., "Deep learning with convolutional neural networks for brain mapping and decoding of movement-related information from the human EEG," arXiv:170.05051v1, Mar. 16, 2017, 58 pp.

(56) References Cited

OTHER PUBLICATIONS

Office Action from U.S. Appl. No. 17/377,763, dated Oct. 13, 2021, 15 pp.
"Visualize Features of a Convolutional Neural Network," MATLAB & Simulink, retrieved from https://www.mathworks.com/help/deeplearning/examples/visualize-features-of-a-convolutional-neural-network.html, Sep. 11, 2019, 7 pp.
U.S. Appl. No. 17/377,763, filed Jul. 16, 2021, Chakravarthy et al.
U.S. Appl. No. 17/377,785, filed Jul. 16, 2021, Pedalty et al.
U.S. Appl. No. 17/389,831, filed Jul. 30, 2021, by Haddad et al.
U.S. Appl. No. 17/383,170, filed Jul. 22, 2021, by Haddad et al.
Isin et al., "Cardiac Arrhythmia Detection Using Deep Learning," Procedia Computer Science vol. 120, 2017 (Applicant points out, in accordance with MPEP 609.04(a), that the year of publication, 2017, is sufficiently earlier than the effective U.S. filing date, so that the particular month of publication is not in issue.) pp. 268-275.
Arrobo et al., "An Innovative Wireless Cardiac Rhythm Management (iCRM) System," Computer Science, 2014 Wireless Telecommunications Symposium, Jun. 2014, 5 pp.
Swerdlow et al., "An Innovative Wireless Cardiac Rhythm Management (iCRM) System," Advances in Arrhythmia and Electrophysiology, vol. 7, No. 6, Dec. 2014, pp. 1237-1261.
Wartzek et al., "ECG on the Road: Robust and Unobtrusive Estimation of Heart Rate," IEEE Transactions on Biomedical Engineering, vol. 58, No. 11, Nov. 2011, pp. 3112-3120.
Chen, Electrocardiogram Recognition Based on Variational AutoEncoder, Aug. 29, 2018, Machine Learning and Biometrics. IntechOpen (Year: 2018).
Final Office Action from U.S. Appl. No. 17/377,763, dated Feb. 18, 2022, 15 pp.
Response to Office Action dated Oct. 13, 2021, from U.S. Appl. No. 17/377,763, filed Jan. 11, 2022, 17 pp.
Swerdlow et al., "Troubleshooting Implanted Cardioverter Defibrillator Sensing Problems I," Advances in Arrhythmia and Electrophysiology, vol. 7, No. 6, Dec. 2014, pp. 1237-1261.
Advisory Action from U.S. Appl. No. 17/377,763, dated Apr. 29, 2022, 3 pp.
Response to Final Office Action dated Feb. 18, 2022, from U.S. Appl. No. 17/377,763, filed Apr. 18, 2022, 6 pp.
U.S. Appl. No. 16/832,732, filed Mar. 27, 2020 by Chakravarthy et al.
Bresnick, "Machine Learning Algorithm Outperforms Cardiologists Reading EKGs", Health IT Analytics, Jul. 12, 2017, p. 5.
Response to Final Office Action dated Feb. 18, 2022, from U.S. Appl. No. 17/377,763, filed Jun. 21, 2022, 22 pp.
Corrected Notice of Allowance from U.S. Appl. No. 17/377,763 dated Aug. 5, 2022, 2 pp.
Notice of Allowance from U.S. Appl. No. 17/377,763 dated Jul. 28, 2022, 8 pp.
Office Action from U.S. Appl. No. 16/850,699 dated Jul. 28, 2022, 22 pp.
Office Action from U.S. Appl. No. 16/851,603 dated Nov. 3, 2022, 13 pp.
Andersen et al., "A Deep Learning Approach for Real-Time Detection of Atrial Fibrillation," Expert Systems with Applications, vol. 114, Aug. 14, 2018, pp. 465-473.
Fawaz et al., "Deep learning for time series classification: a review," Irirmas, Universite Haute Alsace, Dec. 7, 2018, 53 pp.
Habibzadeh et al., "On Determining the Most Appropriate Test Cut-Off Value: the Case of Tests with Continuous Results," Biochemia Medica, Oct. 15, 2016, pp. 297-307.
Lau et al., "Connecting the Dots: From Big Data to Healthy Heart," Circulation, vol. 134, No. 5, Aug. 2, 2017, 5 pp.
Notice of Allowance from U.S. Appl. No. 16/851,603 dated Feb. 22, 2023, 9 pp.
Response to Office Action dated Nov. 3, 2022 from U.S. Appl. No. 16/851,603, filed Feb. 3, 2023, 15 pp.
Schwab et al., "Beat by Beat: Classifying Cardiac Arrhythmias with Recurrent Neural Networks," 2017 Computing in Cardiology (CinC), vol. 44, Oct. 24, 2017, 4 pp.
Witten et al., "Data mining: Practical Machine Learning Tools and Techniques," Third Edition, Morgan Kaufmann, Feb. 3, 2011, 665 pp.

\* cited by examiner ical lead wires placed within the heart. If an arrhythmia is
ARRHYTHMIA DETECTION WITH FEATURE DELINEATION AND MACHINE LEARNING This application is a continuation of U.S. patent application Ser. No. 16/850,699, which was filed Apr. 16, 2020, which claims the benefit of U.S. Provisional Application No. 62/843,738 which was filed on May 6, 2019. The entire content of application Ser. No. 16/850,699 and Application No. 62/843,738 is incorporated herein by reference.

FIELD

This disclosure generally relates to medical devices and, more particularly, to implantable medical devices.

BACKGROUND

Malignant tachyarrhythmia, for example, ventricular fibrillation, is an uncoordinated contraction of the cardiac muscle of the ventricles in the heart, and is the most commonly identified arrhythmia in cardiac arrest patients. If this arrhythmia continues for more than a few seconds, it may result in cardiogenic shock and cessation of effective blood circulation. Consequently, sudden cardiac death (SCD) may result in a matter of minutes.

In patients with a high risk of ventricular fibrillation, the use of an implantable medical device (IMD), such as an implantable cardioverter defibrillator (ICD), has been shown to be beneficial at preventing SCD. An ICD is a battery powered electrical shock device, that may include an electrical housing electrode (sometimes referred to as a can electrode), that is typically coupled to one or more electrical lead wires placed within the heart. If an arrhythmia is sensed, the ICD may send a pulse via the electrical lead wires to shock the heart and restore its normal rhythm. Some ICDs have been configured to attempt to terminate detected tachyarrhythmias by delivery of anti-tachycardia pacing (ATP) prior to delivery of a shock. Additionally, ICDs have been configured to deliver relatively high magnitude post-shock pacing after successful termination of a tachyarrhythmia with a shock, in order to support the heart as it recovers from the shock. Some ICDs also deliver bradycardia pacing, cardiac resynchronization therapy (CRT), or other forms of pacing.

Other types of medical devices may be used for diagnostic purposes. For instance, an implanted or non-implanted medical device may monitor a patient's heart. A user, such as a physician, may review data generated by the medical device for occurrences of cardiac arrhythmias, e.g., atrial or ventricular tachyarrhythmia, or asystole. The user may diagnose a medical condition of the patient based on the identified occurrences of the cardiac arrhythmias.

SUMMARY

In accordance with the techniques of the disclosure, a medical device system is set forth herein that uses both feature delineation and machine learning to detect and classify cardiac arrhythmia in a patient. For example, a computing device receives cardiac electrogram data of a patient sensed by an implantable medical device. The computing device obtains, via feature-based delineation of the cardiac electrogram data, a first classification of arrhythmia in the patient. The computing device applies a machine learning model to the received cardiac electrogram data to obtain a second classification of arrhythmia in the patient. As one example, the computing device uses the first and second classifications to determine whether an episode of arrhythmia has occurred in the patient. As another example, the computing device uses the second classification of arrhythmia obtained from the machine learning model to verify the first classification of arrhythmia in the patient obtained from the feature-based delineation.

In response to determining that an episode of arrhythmia has occurred in the patient, the computing device outputs a report indicating that the episode of arrhythmia has occurred and one or more cardiac features that coincide with the episode of arrhythmia. The computing device may receive, in response to the report, one or more adjustments to one or more parameters used by the implantable medical device to sense the cardiac electrogram data of the patient and perform such adjustments to the implantable medical device.

Furthermore, a medical device system as described herein may classify arrhythmia according to an arrhythmia dictionary. For example, a computing device determines, via feature-based delineation of the cardiac electrogram data of the patient, that an episode of arrhythmia has occurred in the patient. The computing device applies the machine learning model to compare cardiac features coinciding with the episode of arrhythmia with cardiac features of past episodes of arrhythmia in the patient so as to classify the episode of arrhythmia as an episode of arrhythmia of a particular type.

The techniques of the disclosure may provide specific improvements to the field of cardiac arrhythmia detection and classification. For example, the use of both feature delineation and machine learning in conjunction with one another may improve the accuracy of the detection of arrhythmia in a patient over the use of feature delineation or the use of machine learning separately. Furthermore, a medical device system as described herein may allow an implantable medical device of the medical device system to act as a low-granularity filter for detecting arrhythmia in the patient while offloading power-intensive and computationally-complex validation of arrhythmia detection to an external computing device. Therefore, such a system as described herein may provide heightened accuracy in arrhythmia detection and classification, while reducing power usage and improving battery lifetime of devices implanted within the patient. Such improvements may similarly be achieved with lower-power external devices capable of detecting arrhythmias based on cardiac electrical signals, such as patient monitors in the form of a wearable patch, a watch, a necklace, or other device worn by a patient.

In one example, this disclosure describes a method comprising: receiving, by a computing device comprising processing circuitry and a storage medium, cardiac electrogram data of a patient sensed by a medical device; applying, by the computing device, a machine learning model, trained using cardiac electrogram data for a plurality of patients, to the received cardiac electrogram data to determine, based on the machine learning model, that an episode of arrhythmia has occurred in the patient; performing, by the computing device, feature-based delineation of the received cardiac electrogram data to obtain cardiac features present in the cardiac electrogram data; in response to determining that the episode of arrhythmia has occurred in the patient: generating, by the computing device, a report comprising an indication that the episode of arrhythmia has occurred in the patient and one or more of the cardiac features that coincide with the episode of arrhythmia; and outputting, by the computing device and for display, the report comprising the indication that the episode of arrhythmia has occurred in the patient and the one or more of the cardiac features that coincide with the episode of arrhythmia.

In another example, this disclosure describes a method comprising: receiving, by a computing device comprising processing circuitry and a storage medium, cardiac electrogram data of a patient sensed by a medical device; obtaining, by the computing device, a first classification of arrhythmia in the patient determined by feature-based delineation of the received cardiac electrogram data, wherein the feature-based delineation identifies cardiac features present in the cardiac electrogram data; applying, by the computing device, a machine learning model, trained using cardiac electrogram data for a plurality of patients, to the received cardiac electrogram data to determine, based on the machine learning model, a second classification of arrhythmia in the patient; determining, by the computing device and based on the first classification and second classification, that an episode of arrhythmia has occurred in the patient; and in response to determining that the episode of arrhythmia has occurred in the patient: generating, by the computing device, a report comprising an indication that the episode of arrhythmia has occurred in the patient and one or more of the cardiac features that coincide with the episode of arrhythmia; and outputting, by the computing device and for display, the report comprising the indication that the episode of arrhythmia has occurred in the patient and the one or more of the cardiac features that coincide with the episode of arrhythmia.

In another example, this disclosure describes a method comprising: receiving, by a computing device comprising processing circuitry and a storage medium, cardiac electrogram data of a patient sensed by a medical device; obtaining, by the computing device, a first classification of arrhythmia in the patient determined by feature-based delineation of the received cardiac electrogram data, wherein the feature-based delineation identifies first cardiac features present in the cardiac electrogram data that coincide with the first classification of arrhythmia in the patient; determining, by the computing device, that one or more episodes of arrhythmia of the first classification have previously occurred in the patient; in response to determining that the one or more episodes of arrhythmia of the first classification have previously occurred in the patient, applying, by the computing device, a machine learning model, trained using cardiac electrogram data for a plurality of patients, to the received cardiac electrogram data and the first cardiac features present in the cardiac electrogram data to determine, based on the machine learning model, that the first cardiac features are similar to cardiac features that coincide with the one or more episodes of arrhythmia of the first classification that have previously occurred in the patient; in response to determining that the first cardiac features are similar to the cardiac features that coincide with the one or more episodes of arrhythmia of the first classification that have previously occurred in the patient, determining, by the computing device, that an episode of arrhythmia of the first classification has occurred in the patient; and in response to determining that that the episode of arrhythmia of the first classification has occurred in the patient: generating, by the computing device, a report comprising an indication that the episode of arrhythmia of the first classification has occurred in the patient and one or more of the cardiac features that coincide with the episode of arrhythmia; and outputting, by the computing device and for display, the report comprising the indication that the episode of arrhythmia has occurred in the patient and the one or more of the cardiac features that coincide with the episode of arrhythmia.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF DRAWINGS

Like reference characters refer to like elements throughout the figures and description.

DETAILED DESCRIPTION

Figure 1:
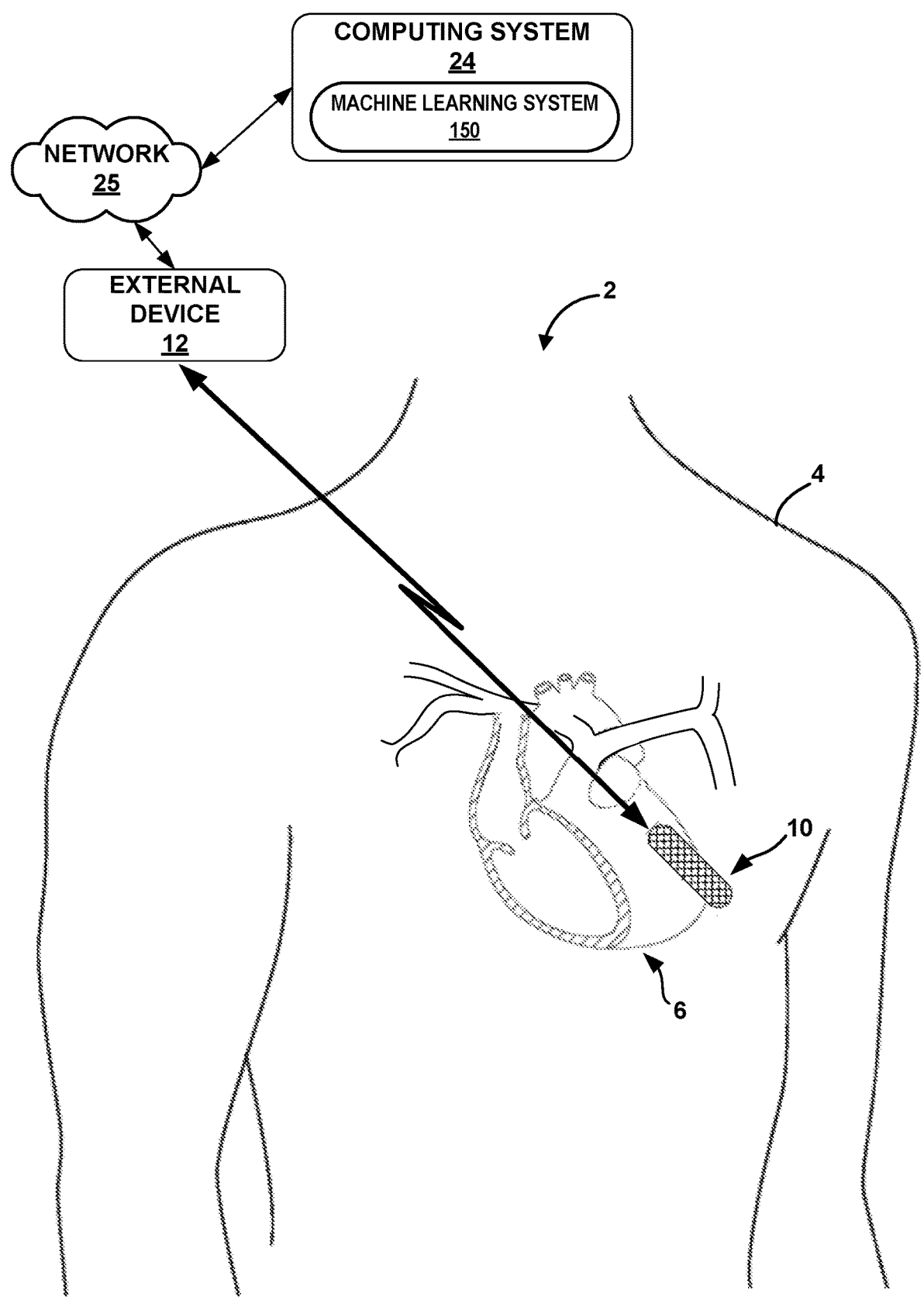
FIG. 1 is a conceptual drawing illustrating an example of a medical device system for predicting cardiac arrhythmia including a leadless implantable medical device and an external device in conjunction with a patient in accordance with the techniques of the disclosure.

Techniques are disclosed for combining multiple decision mechanisms, such as state-of-the-art signal-processing algorithms that perform feature delineation of cardiac electrogram data and machine learning models that process patient data, such as machine learning systems and/or artificial intelligence (AI) algorithms, to analyze single- and multi-channel patient data to perform detection and classification of cardiac arrhythmia in a patient. Such patient data may include, for example, cardiac electrogram data or electrocardiogram (ECG) data.

As described herein, feature delineation refers to the use of features obtained through signal processing for use in detecting or classifying an episode cardiac arrhythmia. Typically, feature delineation involves the use of engineered rules to identify or extract features in cardiac electrogram data, measure characteristics of such features, and use the measurements to detect or classify arrhythmia. For example, feature delineation may be used to identify features such as R-waves, QRS complexes, P-waves, T-waves, rates of such features, intervals between such features, feature morphology, widths, or amplitudes of such features, or other or other types of cardiac features or characteristics of such features not expressly described herein. Feature delineation may include feature extraction, signal filtering, peak detection, refractory analysis, or other types of signal processing, feature engineering, or detection rule development. Feature delineation algorithms may be optimized for real-time, embedded, and low-power applications, such as for use by an implantable medical device. However, feature delineation algorithms may require expert design and feature engineering to accurately detect arrhythmia in a patient.

In contrast to feature delineation techniques for cardiac arrhythmia detection and classification, machine learning techniques may be used for cardiac arrhythmia detection and classification. As described herein, machine learning refers the use of a machine learning model, such as a neural network or deep-learning model, that is trained on training datasets to detect cardiac arrhythmia from cardiac electrogram data. Machine learning techniques may be contrasted from feature delineation in that feature delineation relies on signal processing, which machine learning systems may "learn" underlying features present in cardiac electrogram data indicative of an episode of arrhythmia without requiring knowledge or understanding of the relationship between the features and the episode of arrhythmia on behalf of the system designer.

Machine learning and AI methods for arrhythmia detection may provide a flexible platform to develop arrhythmia detection and classification algorithms with different objectives (e.g., detect atrial fibrillation (AF), exclude cardiac episodes that exhibit no arrhythmia, etc.) without the need for expert design or feature engineering required by feature delineation algorithms. As described in detail herein, techniques, methods, systems, and devices are disclosed that combine feature delineation and machine learning to detect and classify cardiac arrhythmia in a patient in a manner that improves the accuracy and robustness over the use of feature delineation alone, while reducing the power consumption by implantable devices over the use of machine learning alone.

FIG. 1 illustrates the environment of an example medical device system 2 in conjunction with a patient 4 and a heart 6, in accordance with an apparatus and method of certain examples described herein. The example techniques may be used with an IMD 10, which may be leadless and in wireless communication with external device 12, as illustrated in FIG. 1. In some examples, IMD 10 may be coupled to one or more leads. In some examples, IMD 10 may be implanted outside of a thoracic cavity of patient 4 (e.g., subcutaneously in the pectoral location illustrated in FIG. 1). IMD 10 may be positioned near the sternum near and/or just below the level of heart 6.

In some examples, IMD 10 may take the form of a Reveal LINQ™ Insertable Cardiac Monitor (ICM) or a Holter Heart Monitor, both available from Medtronic plc, of Dublin, Ireland. External device 12 may be a computing device configured for use in settings such as a home, clinic, or hospital, and may further be configured to communicate with IMD 10 via wireless telemetry. For example, external device 12 may be coupled to computing system 24 via network 25. Computing system 24 may include a remote patient monitoring system, such as Carelink®, available from Medtronic plc, of Dublin, Ireland. External device 12 may, in some examples, comprise a communication device such as a programmer, an external monitor, or a mobile device, such as a mobile phone, a "smart" phone, a laptop, a tablet computer, a personal digital assistant (PDA), etc.

In some examples, the example techniques and systems described herein may be used with an external medical device in addition to, or instead of 1 MB 10. In some examples, the external medical device is a wearable electronic device, such as the SEEQ™ Mobile Cardiac Telemetry (MCT) system available from Medtronic plc, of Dublin, Ireland, or another type of wearable "smart" electronic apparel, such as a "smart" watch, "smart" patch, or "smart" glasses. Such an external medical device may be positioned externally to patient 4 (e.g., positioned on the skin of patient 4) and may carry out any or all of the functions described herein with respect to IMD 10.

In some examples, a user, such as a physician, technician, surgeon, electro-physiologist, or other clinician, may interact with external device 12 to retrieve physiological or diagnostic information from IMD 10. In some examples, a user, such as patient 4 or a clinician as described above, may also interact with external device 12 to program IMD 10, e.g., select or adjust values for operational parameters of IMD 10. In some examples, external device 12 acts as an access point to facilitate communication with IMD 10 via network 25, e.g., by computing system 24. Computing system 24 may comprise computing devices configured to allow a user to interact with IMD 10 via network 25.

In some examples, computing system 24 includes at least one of a handheld computing device, computer workstation, server or other networked computing device, smartphone, tablet, or external programmer that includes a user interface for presenting information to and receiving input from a user. In some examples, computing system 24 may include one or more devices that implement a machine learning system 150, such as neural network, a deep learning system, or other type of predictive analytics system. A user, such as a physician, technician, surgeon, electro-physiologist, or other clinician, may interact with computing system 24 to retrieve physiological or diagnostic information from IMD 10. A user may also interact with computing system 24 to program IMD 10, e.g., select values for operational parameters of the 1 MB. Computing system 24 may include a processor configured to evaluate EGM and/or other sensed signals transmitted from IMD 10 to computing system 24.

Network 25 may include one or more computing devices (not shown), such as one or more non-edge switches, routers, hubs, gateways, security devices such as firewalls, intrusion detection, and/or intrusion prevention devices, servers, computer terminals, laptops, printers, databases, wireless mobile devices such as cellular phones or personal digital assistants, wireless access points, bridges, cable modems, application accelerators, or other network devices. Network 25 may include one or more networks administered by service providers, and may thus form part of a large-scale public network infrastructure, e.g., the Internet. Network 25 may provide computing devices, such as computing system 24 and IMD 10, access to the Internet, and may provide a communication framework that allows the computing devices to communicate with one another. In some examples, network 25 may be a private network that provides a communication framework that allows computing system 24, IMD 10, and/or external device 12 to communicate with one another but isolates one or more of computing system 24, IMD 10, or external device 12 from devices external to network 25 for security purposes. In some examples, the communications between computing system 24, IMD 10, and external device 12 are encrypted.

External device 12 and computing system 24 may communicate via wireless communication over network 25 using any techniques known in the art. In some examples, computing system 24 is a remote device that communicates with external device 12 via an intermediary device located in network 25, such as a local access point, wireless router, or gateway. While in the example of FIG. 1, external device 12 and computing system 24 communicate over network 25, in some examples, external device 12 and computing system 24 communicate with one another directly. Examples of communication techniques may include, for example, communication according to the Bluetooth® or BLE protocols.

Other communication techniques are also contemplated. Computing system 24 may also communicate with one or more other external devices using a number of known communication techniques, both wired and wireless.

In any such examples, processing circuitry of medical device system 2 may transmit patient data, including cardiac electrogram data, for patient 4 to a remote computer (e.g., external device 12). In some examples, processing circuitry of medical device system 2 may transmit a determination that patient 4 is undergoing an episode of cardiac arrhythmia such as an episode of bradycardia, tachycardia, atrial fibrillation, ventricular fibrillation, or AV Block.

External device 12 may be a computing device (e.g., used in a home, ambulatory, clinic, or hospital setting) to communicate with IMD 10 via wireless telemetry. External device 12 may include or be coupled to a remote patient monitoring system, such as Carelink®, available from Medtronic plc, of Dublin, Ireland. In some examples, external device 12 may receive data, alerts, patient physiological information, or other information from IMD 10.

External device 12 may be used to program commands or operating parameters into IMD 10 for controlling its functioning (e.g., when configured as a programmer for IMD 10). In some examples, external device 12 may be used to interrogate IMD 10 to retrieve data, including device operational data as well as physiological data accumulated in IMD memory. Such interrogation may occur automatically according to a schedule and/or may occur in response to a remote or local user command. Programmers, external monitors, and consumer devices are examples of external devices 12 that may be used to interrogate IMD 10. Examples of communication techniques used by IMD 10 and external device 12 include radiofrequency (RF) telemetry, which may be an RF link established via Bluetooth, WiFi, or medical implant communication service (MICS). In some examples, external device 12 may include a user interface configured to allow patient 4, a clinician, or another user to remotely interact with IMD 10. In some such examples, external device 12, and/or any other device of medical device system 2, may be a wearable device, (e.g., in the form of a watch, necklace, or other wearable item).

Medical device system 2 is an example of a medical device system configured to perform cardiac arrhythmia detection, verification, and reporting. In accordance with the techniques of the disclosure, medical device system 2 implements machine learning arrhythmia detection and feature delineation to detect and classify cardiac arrhythmias in patient 4. Additional examples of the one or more other implanted or external devices may include an implanted, multi-channel cardiac pacemaker, ICD, IPG, leadless (e.g., intracardiac) pacemaker, extravascular pacemaker and/or ICD, or other IMD or combination of such IMDs configured to deliver CRT to heart 6, an external monitor, an external therapy delivery device such as an external pacing or electrical stimulation device, or a drug pump.

Communication circuitry of each of the devices of medical device system 2 (e.g., IMD 10 and external device 12) may enable the devices to communicate with one another. In addition, although one or more sensors (e.g., electrodes) are described herein as being positioned on a housing of IMD 10, in other examples, such sensors may be positioned on a housing of another device implanted in or external to patient 4. In such examples, one or more of the other devices may include processing circuitry configured to receive signals from the electrodes or other sensors on the respective devices and/or communication circuitry configured to transmit the signals from the electrodes or other sensors to another device (e.g., external device 12) or server.

In accordance with the techniques of the disclosure, medical device system 2 uses both feature delineation and machine learning to detect and classify cardiac arrhythmia in patient 4. For example, computing system 24 receives cardiac electrogram data of patient 4 sensed by implantable medical device 10. Computing system 24 obtains, via feature-based delineation of the cardiac electrogram data, a first classification of arrhythmia in patient 4. In some examples, the feature-based delineation of the cardiac electrogram data to determine the first classification of arrhythmia in patient 4 is performed by any one of IMD 10, external device 12, or computing system 24. Machine learning system 150 applies a machine learning model to the received cardiac electrogram data to obtain a second classification of arrhythmia in patient 4. In one example, the machine learning model is a deep-learning model. As one example, computing system 24 uses the first and second classifications to determine whether an episode of arrhythmia has occurred in patient 4. As another example, computing system 24 uses the second classification of arrhythmia obtained from machine learning system 150 to verify the first classification of arrhythmia in patient 4 obtained from the feature-based delineation.

In response to determining that an episode of arrhythmia has occurred in patient 4, computing system 24 outputs a report indicating that the episode of arrhythmia has occurred and one or more cardiac features that coincide with the episode of arrhythmia. Computing system 24 may receive, in response to the report, one or more adjustments to one or more parameters used by implantable medical device 10 to sense the cardiac electrogram data of patient 4 and perform such adjustments to implantable medical device 10 for subsequent sensing.

Furthermore, medical device system 2 may classify arrhythmia according to an arrhythmia dictionary. As described in more detail below, computing system 24 determines, via feature-based delineation of the cardiac electrogram data of patient 4, that an episode of arrhythmia has occurred in patient 4. Machine learning system 150 applies a machine learning model to compare cardiac features coinciding with the episode of arrhythmia with cardiac features of past episodes of arrhythmia in patient 4 so as to classify the episode of arrhythmia as an episode of arrhythmia of a particular type.

The techniques of the disclosure may provide specific improvements to the field of cardiac arrhythmia detection and classification. For example, the use of both feature delineation and machine learning in conjunction with one another may improve the accuracy of the detection of arrhythmia in patient 4 over the use of feature delineation or the use of machine learning separately. Furthermore, medical device system 2 as described herein may allow implantable medical device 10 to act as a low-granularity filter for detecting arrhythmia in patient 4 while offloading power-intensive and computationally-complex validation of arrhythmia detection to an external device, such as external device 12 or computing system 24. Therefore, system 2, as described herein, may provide heightened accuracy in the detection and classification of arrhythmia in patient 4, while reducing power usage and improving battery lifetime of IMD 10.

Figure 2:
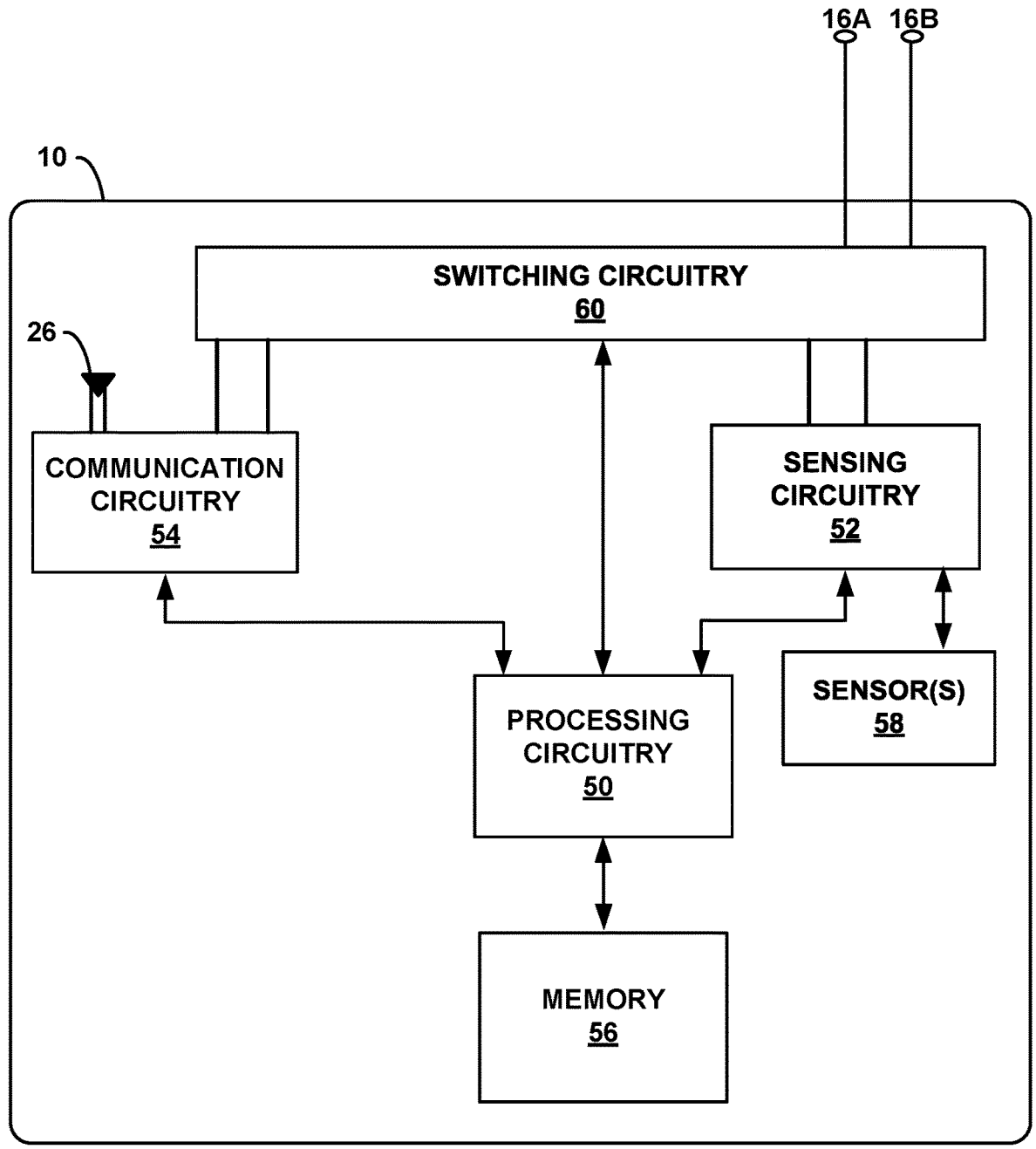
FIG. 2 is a block diagram illustrating an example of the leadless implantable medical device of FIG. 1.

FIG. 2 is a block diagram illustrating an example of the leadless implantable medical device of FIG. 1. As shown in FIG. 2, IMD 10 includes processing circuitry 50 sensing circuitry 52, communication circuitry 54, memory 56, sensors 58, switching circuitry 60, and electrodes 16A, 16B (hereinafter "electrodes 16"), one or more of which may be disposed within a housing of IMD 10. In some examples, memory 56 includes computer-readable instructions that, when executed by processing circuitry 50, cause IMD 10 and processing circuitry 50 to perform various functions attributed to IMD 10 and processing circuitry 50 herein. Memory 56 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital media.

Processing circuitry 50 may include fixed function circuitry and/or programmable processing circuitry. Processing circuitry 50 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware, or any combination thereof.

Sensing circuitry 52 and communication circuitry 54 may be selectively coupled to electrodes 16A, 16B via switching circuitry 60 as controlled by processing circuitry 50. Sensing circuitry 52 may monitor signals from electrodes 16A, 16B in order to monitor electrical activity of a heart of patient 4 of FIG. 1 and produce cardiac electrogram data for patient 4. In some examples, processing circuitry 50 may perform feature delineation of the sensed cardiac electrogram data to detect an episode of cardiac arrhythmia of patient 4. In some examples, processing circuitry 50 transmits, via communication circuitry 54, the cardiac electrogram data for patient 4 to an external device, such as external device 12 of FIG. 1. For example, IMD 10 sends digitized cardiac electrogram data to network 25 for processing by machine learning system 150 of FIG. 1. In some examples, IMD 10 transmits one or more segments of the cardiac electrogram data in response to detecting, via feature delineation, an episode of arrhythmia. In another example, IMD 10 transmits one or more segments of the cardiac electrogram data in response to instructions from external device 12 (e.g., when patient 4 experiences one or more symptoms of arrhythmia and inputs a command to external device 12 instructing IMD 10 to upload the cardiac electrogram data for analysis by a monitoring center or clinician). The cardiac electrogram data may be processed by machine learning system 150 to detect and classify cardiac arrhythmia as described in detail below.

In some examples, IMD 10 performs feature delineation of the sensed cardiac electrogram data as described in more detail below. In some examples, the feature delineation performed by IMD 10 is of a reduced complexity so as to conserve power in IMD 10. This may enable IMD 10 to perform initial or preliminary detection of cardiac arrhythmia. As described in detail below, computing system 24 may additionally perform feature delineation of the cardiac electrogram data sensed by IMD 10, as well as apply machine learning system 150 to the cardiac electrogram data. Computing system 24 may possess more computational resources and less power restrictions over IMD 10, thereby allowing computing system 24 to perform a more comprehensive and detailed analysis of the cardiac electrogram data so as to more accurately detect cardiac arrhythmia. By shifting the computational burden from IMD 10 to computation system 24, the techniques of the disclosure may serve to reduce the power consumption of IMD 10 while increasing the accuracy in arrhythmia detection.

In some examples, IMD 10 includes one or more sensors 58, such as one or more accelerometers, microphones, and/or pressure sensors. Sensing circuitry 52 may monitor signals from sensors 58 and transmit patient data obtained from sensors 58, to an external device, such as external device 12 of FIG. 1, for analysis. In some examples, sensing circuitry 52 may include one or more filters and amplifiers for filtering and amplifying signals received from one or more of electrodes 16A, 16B and/or other sensors 58. In some examples, sensing circuitry 52 and/or processing circuitry 50 may include a rectifier, filter and/or amplifier, a sense amplifier, comparator, and/or analog-to-digital converter.

Communication circuitry 54 may include any suitable hardware, firmware, software, or any combination thereof for communicating with another device, such as external device 12 or another medical device or sensor, such as a pressure sensing device. Under the control of processing circuitry 50, communication circuitry 54 may receive downlink telemetry from, as well as send uplink telemetry to, external device 12 or another device with the aid of an internal or external antenna, e.g., antenna 26. In some examples, communication circuitry 54 may communicate with external device 12. In addition, processing circuitry 50 may communicate with a networked computing device via an external device (e.g., external device 12) and a computer network, such as the Medtronic CareLink® Network developed by Medtronic, plc, of Dublin, Ireland.

A clinician or other user may retrieve data from IMD 10 using external device 12, or by using another local or networked computing device configured to communicate with processing circuitry 50 via communication circuitry 54. The clinician may also program parameters of IMD 10 using external device 12 or another local or networked computing device. In some examples, the clinician may select one or more parameters defining how IMD 10 senses cardiac electrogram data of patient 4.

One or more components of IMD 10 may be coupled a power source (not depicted in FIG. 2), which may include a rechargeable or non-rechargeable battery positioned within a housing of IMD 10. A non-rechargeable battery may be selected to last for several years, while a rechargeable battery may be inductively charged from an external device, e.g., on a daily or weekly basis.

In accordance with the techniques of the disclosure, processing circuitry 50 senses, with sensing circuitry 52 and via electrodes 16, cardiac electrogram data of patient 4. In some examples, the cardiac electrogram data is an ECG for patient 4. Processing circuitry 50 performs, via feature delineation, of the cardiac electrogram data to obtain one or more cardiac features present in the cardiac electrogram data. In some examples, the feature delineation includes one or more of QRS detection, refractory processing, noise processing, or delineation of the cardiac electrogram data. For example, processing circuitry 50 receives a raw signal from via sensing circuitry 50 and/or sensors 58, and extracts one or more cardiac features from the raw signal. In some examples, processing circuitry 50 identifies one or more cardiac features, such as one or more of a mean heartrate of the patient, a minimum heartrate of the patient, a maximum heartrate of the patient, a PR interval of a heart of the patient, a variability of heartrate of the patient, one or more amplitudes of one or more features of an electrocardiogram (ECG) of the patient, or an interval between the or more features of the ECG of the patient, a T-wave alternans, QRS morphology measures, or other types of cardiac features not expressly described herein.

As one example, processing circuitry 50 identifies one or more features of a T-wave of an electrocardiogram of patient 4 and applies a model to the one or more identified features to detect an episode of cardiac arrhythmia in patient 4. In some examples, the one or more identified features are one or more amplitudes of the T-wave. In some examples, the one or more identified features are a frequency of the T-wave. In some examples, the one or more identified features include at least an amplitude of the T-wave and a frequency of the T-wave. In some examples, processing circuitry 50 identifies one or more relative changes in the one or more identified features that are indicative of an episode subsequent cardiac arrhythmia in patient 4. In some examples, processing circuitry 50 identifies one or more interactions between multiple identified features that are indicative of an episode of cardiac arrhythmia in patient 4. In some examples, processing circuitry 50 analyzes patient data that represents one or more values that are averaged over a short-term period of time (e.g., about 30 minutes to about 60 minutes). For example, the patient data may include one or more of an average frequency or an average amplitude of a T-wave of an electrocardiogram of patient 4 to detect the episode of cardiac arrhythmia.

Processing circuitry 50 may further apply such feature delineation to determine that the one or more cardiac features are indicative of an episode of cardiac arrhythmia. Processing circuitry 50 further applies feature delineation to classify the detected episode of cardiac arrhythmia as an episode of cardiac arrhythmia of a particular type (e.g., bradycardia, tachycardia, atrial fibrillation, ventricular fibrillation, or AV Block). Processing circuitry 50 transmits, via communication circuitry 54, one or more of the cardiac electrogram data, the one or more cardiac features present in the cardiac electrogram data, an indication of the detected episode of cardiac arrhythmia, or an indication of the classification of the detected episode of cardiac arrhythmia, to external device 12.

Although described herein in the context of example IMD 10 that senses cardiac electrogram data of patient 4, the techniques for cardiac arrhythmia detection disclosed herein may be used with other types of devices. For example, the techniques may be implemented with an extra-cardiac defibrillator coupled to electrodes outside of the cardiovascular system, a transcatheter pacemaker configured for implantation within the heart, such as the Micra™ transcatheter pacing system commercially available from Medtronic PLC of Dublin Ireland, an insertable cardiac monitor, such as the Reveal LINQ™ ICM, also commercially available from Medtronic PLC, a neurostimulator, a drug delivery device, a medical device external to patient 4, a wearable device such as a wearable cardioverter defibrillator, a fitness tracker, or other wearable device, a mobile device, such as a mobile phone, a "smart" phone, a laptop, a tablet computer, a personal digital assistant (PDA), or "smart" apparel such as "smart" glasses, a "smart" patch, or a "smart" watch.

Figure 3:
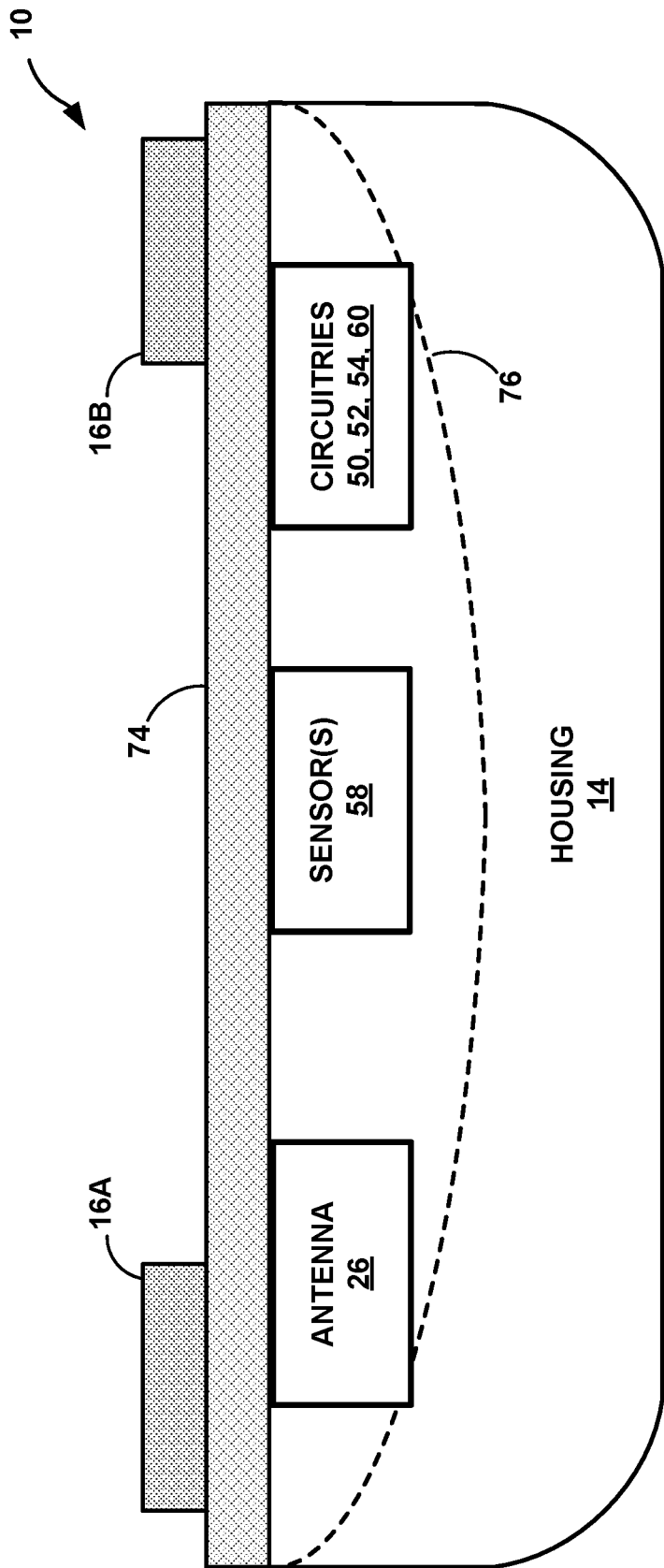
FIG. 3 is a block diagram illustrating another example of the leadless implantable medical device of FIG. 1.

FIG. 3 is a block diagram illustrating another example of the leadless implantable medical device of FIG. 1. The components of FIG. 3 may not necessarily be drawn to scale, but instead may be enlarged to show detail. Specifically, FIG. 3 is a block diagram of a top view of an example configuration of an IMD 10 of FIG. 1.

FIG. 3 is a conceptual drawing illustrating an example IMD 10 that may include components substantially similar to IMD 10 of FIG. 1. In addition to the components illustrated in FIGS. 1 and 2, the example of IMD 10 illustrated in FIG. 3 also may include a wafer-scale insulative cover 74, which may help insulate electrical signals passing between electrodes 16A, 16B on housing 14 and processing circuitry 50. In some examples, insulative cover 74 may be positioned over an open housing 14 to form the housing for the components of IMD 10B. One or more components of IMD 10B (e.g., antenna 26, processing circuitry 50, sensing circuitry 52, communication circuitry 54, and/or switching circuitry 60) may be formed on a bottom side of insulative cover 74, such as by using flip-chip technology. Insulative cover 74 may be flipped onto housing 14. When flipped and placed onto housing 14, the components of IMD 10 formed on the bottom side of insulative cover 74 may be positioned in a gap 78 defined by housing 14. Housing 14 may be formed from titanium or any other suitable material (e.g., a biocompatible material), and may have a thickness of about 200 micrometers to about 500 micrometers. These materials and dimensions are examples only, and other materials and other thicknesses are possible for devices of this disclosure.

In some examples, IMD 10 collects, via sensing circuitry 50 and/or sensors 58, patient data of patient 4 including cardiac electrogram data. Sensors 58 may include one or more sensors, such as one or more accelerometers, pressure sensors, optical sensors for O2 saturation, etc. In some examples, the patient data includes one or more of an activity level of the patient, a heartrate of the patient, a posture of the patient, a cardiac electrogram of the patient, a blood pressure of the patient, accelerometer data for the patient, or other types of patient parametric data. IMD 10 uploads, via communication circuitry 54, the patient data to external device 12, which may in turn upload such data to computing system 24 over network 25. In some examples, IMD 10 uploads the patient data to computing system 24 on a daily basis. In some examples, the patient data includes one or more values that represent average measurements of patient 4 over a long-term time period (e.g., about 24 hours to about 48 hours). In this example, IMD 10 both uploads the patient data to computing system 24 and performs short-term monitoring of patient 4 (as described below). However, in other examples, the medical device that processes the patient data to detect and/or classify arrhythmia in patient 4 is different from the medical device that performs short-term monitoring of patient 4.

Figure 4:
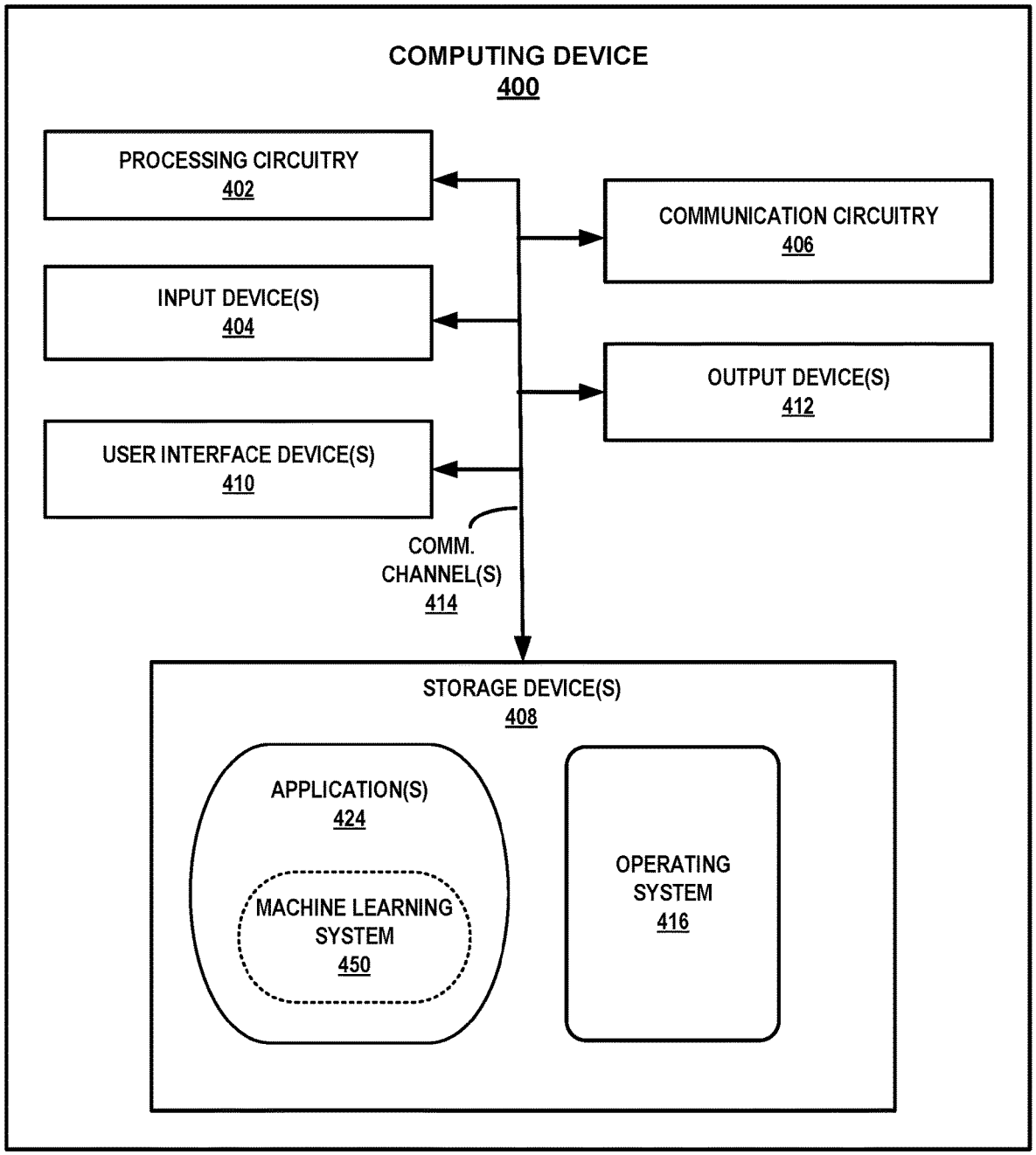
FIG. 4 is a block diagram illustrating an example computing device that operates in accordance with one or more techniques of the present disclosure.

FIG. 4 is a block diagram illustrating an example computing device 400 that operates in accordance with one or more techniques of the present disclosure. In one example, computing device 400 is an example implementation of computing system 24 of FIG. 1. In one example, computing device 400 includes processing circuitry 402 for executing applications 424 that include machine learning system 450 or any other applications described herein. Although shown in FIG. 4 as a stand-alone computing device 400 for purposes of example, computing device 400 may be any component or system that includes processing circuitry or other suitable computing environment for executing software instructions and, for example, need not necessarily include one or more elements shown in FIG. 4 (e.g., input devices 404, communication circuitry 406, user interface devices 410, or output devices 412; and in some examples components such as storage device(s) 408 may not be co-located or in the same chassis as other components). In some examples, computing device 400 may be a cloud computing system distributed across a plurality of devices.

As shown in the example of FIG. 4, computing device 400 includes processing circuitry 402, one or more input devices 404, communication circuitry 406, one or more storage devices 408, user interface (UI) device(s) 410, and one or more output devices 412. Computing device 400, in one example, further includes one or more application(s) 424 such as machine learning system 450, and operating system 416 that are executable by computing device 400. Each of components 402, 404, 406, 408, 410, and 412 are coupled (physically, communicatively, and/or operatively) for inter-component communications. In some examples, communication channels 414 may include a system bus, a network connection, an inter-process communication data structure, or any other method for communicating data. As one example, components 402, 404, 406, 408, 410, and 412 may be coupled by one or more communication channels 414.

Processing circuitry 402, in one example, is configured to implement functionality and/or process instructions for execution within computing device 400. For example, processing circuitry 402 may be capable of processing instructions stored in storage device 408. Examples of processing circuitry 402 may include, any one or more of a microprocessor, a controller, a digital signal processor (DSP), an application specific integrated circuit (ASIC), a field-programmable gate array (FPGA), or equivalent discrete or integrated logic circuitry.

One or more storage devices 408 may be configured to store information within computing device 400 during operation. Storage device 408, in some examples, is described as a computer-readable storage medium. In some examples, storage device 408 is a temporary memory, meaning that a primary purpose of storage device 408 is not long-term storage. Storage device 408, in some examples, is described as a volatile memory, meaning that storage device 408 does not maintain stored contents when the computer is turned off. Examples of volatile memories include random access memories (RAM), dynamic random access memories (DRAM), static random access memories (SRAM), and other forms of volatile memories known in the art. In some examples, storage device 408 is used to store program instructions for execution by processing circuitry 402. Storage device 408, in one example, is used by software or applications 424 running on computing device 400 to temporarily store information during program execution.

Storage devices 408, in some examples, also include one or more computer-readable storage media. Storage devices 408 may be configured to store larger amounts of information than volatile memory. Storage devices 408 may further be configured for long-term storage of information. In some examples, storage devices 408 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Computing device 400, in some examples, also includes communication circuitry 406. Computing device 400, in one example, utilizes communication circuitry 406 to communicate with external devices, such as IMD 10 and external device 12 of FIG. 1. Communication circuitry 406 may include a network interface card, such as an Ethernet card, an optical transceiver, a radio frequency transceiver, or any other type of device that can send and receive information. Other examples of such network interfaces may include 3G and WiFi radios.

Computing device 400, in one example, also includes one or more user interface devices 410. User interface devices 410, in some examples, are configured to receive input from a user through tactile, audio, or video feedback. Examples of user interface devices(s) 410 include a presence-sensitive display, a mouse, a keyboard, a voice responsive system, video camera, microphone, or any other type of device for detecting a command from a user. In some examples, a presence-sensitive display includes a touch-sensitive screen.

One or more output devices 412 may also be included in computing device 400. Output device 412, in some examples, is configured to provide output to a user using tactile, audio, or video stimuli. Output device 412, in one example, includes a presence-sensitive display, a sound card, a video graphics adapter card, or any other type of device for converting a signal into an appropriate form understandable to humans or machines. Additional examples of output device 412 include a speaker, a cathode ray tube (CRT) monitor, a liquid crystal display (LCD), or any other type of device that can generate intelligible output to a user.

Computing device 400 may include operating system 416. Operating system 416, in some examples, controls the operation of components of computing device 400. For example, operating system 416, in one example, facilitates the communication of one or more applications 424 and long-term prediction module 450 with processing circuitry 402, communication circuitry 406, storage device 408, input device 404, user interface devices 410, and output device 412.

Application 422 may also include program instructions and/or data that are executable by computing device 400. Example application(s) 422 executable by computing device 400 may include machine learning system 450. Other additional applications not shown may alternatively or additionally be included to provide other functionality described herein and are not depicted for the sake of simplicity.

In accordance with the techniques of the disclosure, computing device 400 applies a machine learning model of machine learning system 450 to patient data sensed by IMD 10 to detect and classify an episode of arrhythmia occurring in patient 10. In some examples, machine learning system 450 is an example of machine learning system 150 of FIG. 1.

In some examples, the machine learning model implemented by machine learning system 450 is trained with training data that comprises cardiac electrogram data for a plurality of patients labeled with descriptive metadata. For example, during a training phase, machine learning system 450 processes a plurality of ECG waveforms. Typically, the plurality of ECG waveforms are from a plurality of different patients. Each ECG waveform is labeled with one or more episodes of arrhythmia of one or more types. For example, a training ECG waveform may include a plurality of segments, each segment labeled with a descriptor that specifies an absence of arrhythmia or a presence of an arrhythmia of a particular classification (e.g., bradycardia, tachycardia, atrial fibrillation, ventricular fibrillation, or AV Block). In some examples, a clinician labels the presence of arrhythmia in each ECG waveform by hand. In some examples, the presence of arrhythmia in each ECG waveform is labeled according to classification by a feature delineation algorithm. Machine learning system 450 may operate to convert the training data into vectors and tensors (e.g., multi-dimensional arrays) upon which machine learning system 450 may apply mathematical operations, such as linear algebraic, nonlinear, or alternative computation operations. Machine learning system 450 uses the training data 104 to teach the machine learning model to weigh different features depicted in the cardiac electrogram data. In some examples, machine learning system 450 uses the cardiac electrogram data to teach the machine learning model to apply different coefficients that represent one or more features in a cardiac electrogram as having more or less importance with respect to an occurrence of a cardiac arrhythmia of a particular classification. By processing numerous such ECG waveforms labeled with episodes of arrhythmia, machine learning system 450 may build and train a machine learning model to receive cardiac electrogram data from a patient, such as patient 4 of FIG. 1, that machine learning system 450 has not previously analyzed, and process such cardiac electrogram data to detect the presence or absence of arrhythmia of different classifications in the patient with a high degree of accuracy. Typically, the greater the amount of cardiac electrogram data on which machine learning system 450 is trained, the higher the accuracy of the machine learning model in detecting or classifying cardiac arrhythmia in new cardiac electrogram data.

After machine learning system 450 has trained the machine learning model, machine learning system 450 may receive patient data, such as cardiac electrogram data, for a particular patient, such as patient 4. Machine learning system 450 applies the trained machine learning model to the patient data to detect an occurrence of an episode of cardiac arrhythmia in patient 4. Further, machine learning system 450 applies the trained machine learning model to the patient data to classify the episode of cardiac arrhythmia in patient as indicative of a particular type of arrhythmia. In some examples, machine learning system 450 may output a preliminary determination that the episode of cardiac arrhythmia is indicative of a particular type of arrhythmia, as well as an estimate of certainty in the determination. In response to determining that the estimate of certainty in the determination is greater than a predetermined threshold (e.g., 50%, 75%, 90%, 95%, 99%), computing device 400 may classify that the episode of cardiac arrhythmia as the particular type of arrhythmia.

In some examples, machine learning system may process one or more cardiac features of cardiac electrogram data instead of the raw cardiac electrogram data itself. The one or more cardiac features may be obtained via feature delineation performed by IMD 10, as described above. The cardiac features may include, e.g., one or more of a mean heartrate of the patient, a minimum heartrate of the patient, a maximum heartrate of the patient, a PR interval of a heart of the patient, a variability of heartrate of the patient, one or more amplitudes of one or more features of an electrocardiogram (ECG) of the patient, or an interval between the or more features of the ECG of the patient, a T-wave alternans, QRS morphology measures, or other types of cardiac features not expressly described herein. In such example implementations, machine learning system may train the machine learning model via a plurality of training cardiac features labeled with episodes of arrhythmia, instead of the plurality of ECG waveforms labeled with episodes of arrhythmia as described above.

In some examples, machine learning system 450 may apply the machine learning model to other types of data to determine that an episode of arrhythmia has occurred in patient 4. For example, machine learning system 450 may apply the machine learning model to one or more characteristics of cardiac electrogram data that are correlated to arrhythmia in the patient, an activity level of IMD 10, an input impedance of IMD 10, or a battery level of IMD 10.

In further examples, processing circuitry 402 may generate, from the cardiac electrogram data, an intermediate representation of the cardiac electrogram data. For example, processing circuitry 402 may apply one or more signal processing, signal decomposition, wavelet decomposition, filtering, or noise reduction operations to the cardiac electrogram data to generate the intermediate representation of the cardiac electrogram data. In this example, machine learning system 450 processes such an intermediate representation of the cardiac electrogram data to detect and classify an episode of arrhythmia in patient 4. Furthermore, machine learning system may train the machine learning model via a plurality of training intermediate representations labeled with episodes of arrhythmia, instead of the plurality of raw ECG waveforms labeled with episodes of arrhythmia as described above. The use of such intermediate representations of the cardiac electrogram data may allow for the training and development of a lighter-weight, less computationally complex machine learning model by machine learning system 450. Further, the use of such intermediate representations of the cardiac electrogram data may require less iterations and fewer training data to build an accurate machine learning model, as opposed to the use of raw cardiac electrogram data to train the machine learning model.

In some examples, computing system 24 may use machine learning system 150 to detect other types of arrhythmias beyond the ones in detected in the feature delineation screening analysis. For example, arrhythmia detection algorithms for performing feature delineation implemented by low-power devices such as IMD 10 may not be designed to detect less-frequently occurring arrhythmias, such as AV Blocks. Machine learning system 150 may train a machine learning model on large datasets where such arrhythmias are available, thereby providing finer granularity and higher accuracy over feature delineation performed by, e.g., IMD 10 alone. Therefore, the use of machine learning system 150 may expand the arrhythmia diagnosis capability of system 2 by allowing IMD 10 to implement a generic screening algorithm using feature delineation followed by the use of machine learning system 150 that implements a machine learning model that can provide a wider range of arrhythmia detection. After detecting a type of arrhythmia that was not detected by feature delineation, computing system 24 may nevertheless use feature delineation, such as QRS detection, to assist in characterizing and reporting the other types of arrhythmias detected by the machine learning model of machine learning system 150.

In some examples, computing system 24 may tailor machine learning system 150 to the specific use case. For example, machine learning system 150 may implement a machine learning model specific to detecting AV Blocks and bradycardia where patient 4 is a post-TAVR patient. As another example, machine learning system 150 may implement a machine learning model specific to detecting PVCs such that PVC burden may be used to risk-stratify patients who might be indicated for ICDs.

Figure 5:
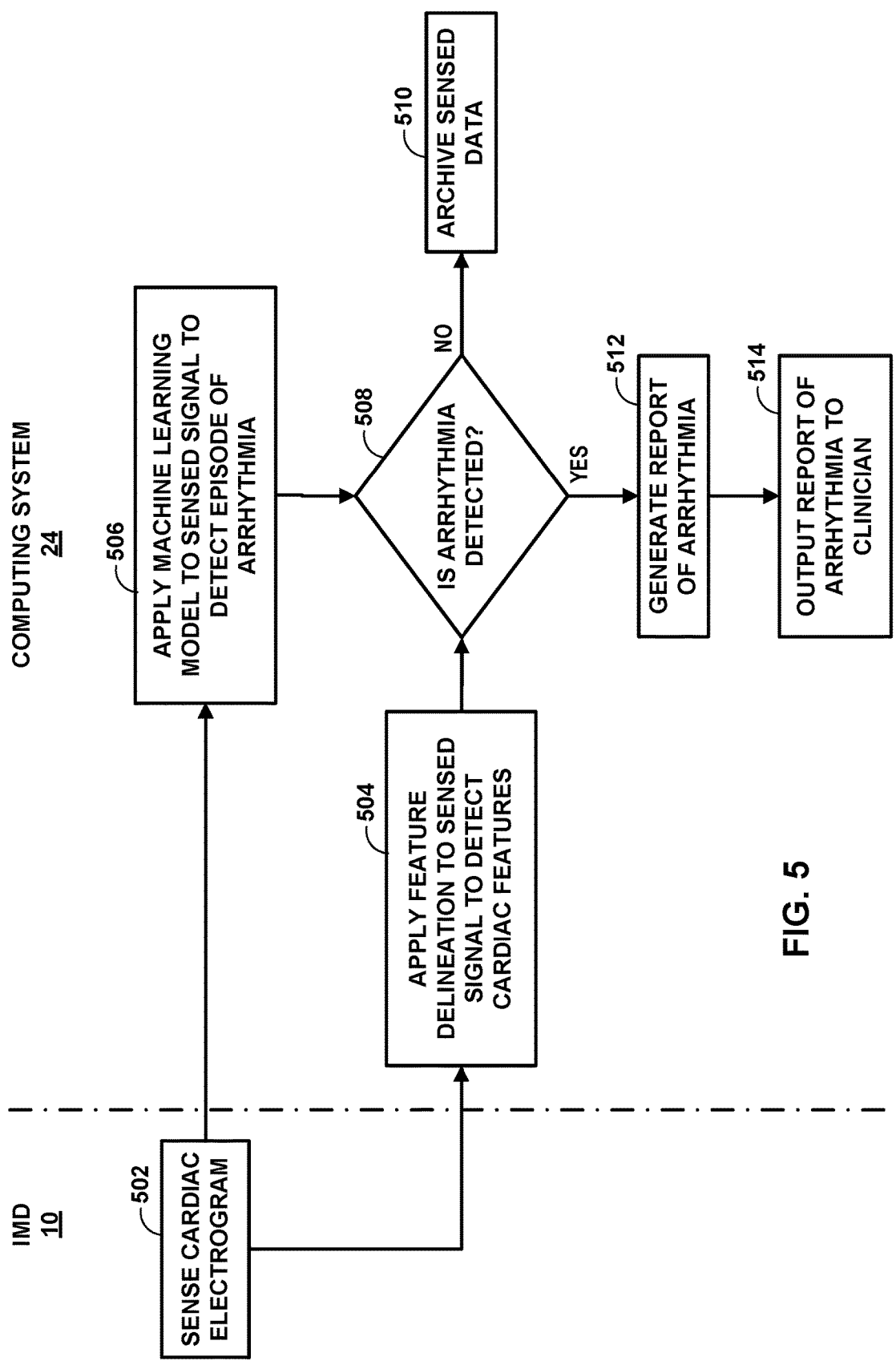
FIG. 5 is a flowchart illustrating an example operation in accordance with the techniques of the disclosure.

FIG. 5 is a flowchart illustrating an example operation in accordance with the techniques of the disclosure. For convenience, FIG. 5 is described with respect to FIG. 1. In some examples, the operation of FIG. 5 is an operation for detecting and classifying cardiac arrhythmia in patient 4. In the operation of FIG. 5, system 2 combines ability of the machine learning model of machine learning system 150 to learn features and perform classification directly from an input with the interpretability provided by the feature delineation algorithms and ECG-processing. In the example operation of FIG. 5, system 2 implements machine learning model of machine learning system 150 in parallel with feature delineation algorithms to perform arrhythmia detection and characterization.

As depicted in FIG. 5, IMD 10 senses cardiac electrogram data of patient 4 (502). The cardiac electrogram data can be, e.g., an episodic ECG of patient 4 or a full-disclosure ECG of patient 4. Further, the cardiac electrogram data of patient 4 may be from a single-channel or multi-channel system. For simplicity, in the example of FIG. 5, the cardiac electrogram data of patient 4 is described as single-channel episodic ECG data.

Machine learning system 150 of computing system 24 applies a machine learning model to the sensed cardiac electrogram to detect an episode of arrhythmia in patient 4 (506). In some examples, the machine learning model is trained with a plurality of ECG episodes annotated by a clinician or a monitoring center for arrhythmias of several different types. In one example, machine learning system 150 applies the machine learning model to take one or several subsegments of a normalized input ECG signal and generates arrhythmia labels and a likelihood of an occurrence of the arrhythmia. In some examples, the machine learning model may be accurate in mapping an input ECG to an output arrhythmia label, but may not provide additional arrhythmia characteristics or identify the specific cardiac features, such as a mean heartrate, a maximum heartrate, P-R interval characteristics, etc., used to make the determination that an episode of arrhythmia has occurred in patient 4. Furthermore, one may be unable to obtain physician-provided notifications or reportable criteria (e.g., that 4 out of 4 heartbeats of patient 4 exhibited a heartrate of less than 30 beats per minute (BPM)) from the output or intermediate states of the machine learning model such that a clinician would be able to make use of the determination that an episode of arrhythmia has occurred in patient 4 for use in providing subsequent therapy to patient 4.

To address this, computing system 24 further applies feature delineation to the cardiac electrogram data to detect one or more cardiac features (504). In some examples, computing system 24 further applies feature delineation to the cardiac electrogram data to detect one or more episodes of arrhythmia. For example, computing system 24 may apply QRS detection delineation and noise flagging (e.g., is the beat noisy or not) to the cardiac electrogram data to provide arrhythmia characteristics and/or cardiac features for detected episodes of arrhythmia (e.g., an average heartrate during an episode of atrial fibrillation, a duration of a pause). Further, computing system 24 may apply feature delineation to guide notification and reporting criteria for system 2. In the example of FIG. 5, computing system 24 performs feature delineation of the cardiac electrogram data. However, in other examples of the techniques of the disclosure, other devices, such as IMD 10, external device 12, or another external medical device, may perform feature delineation of the cardiac electrogram data.

With respect to the example of FIG. 5, computing system applies both machine learning system 150 and feature delineation to determine whether an episode of cardiac arrhythmia is detected in patient 4 (508). If neither machine learning system 150 nor feature delineation detect an episode of cardiac arrhythmia (e.g., "NO" block of 508), then computing system may archive the cardiac electrogram data for subsequent review by a clinician.

If at least one of machine learning system 150 or the feature delineation operation of (504) detect an episode of cardiac arrhythmia (e.g., "YES" block of 508), then computing system may generate a report of the arrhythmia (512) and output the report to a clinician or monitoring center (514). For example, if machine learning system 150 detects an episode of bradycardia and feature delineation performed on the cardiac electrogram data indicates that 4 out of 4 non-noisy heartbeats are less than 30 BPM, then computing system 24 generates a report notifying the physician of the occurrence of the episode of arrhythmia.

In one example, the report includes an indication that the episode of arrhythmia has occurred in the patient and one or more of the cardiac features that coincide with the episode of arrhythmia. In some examples, the report further includes a classification of the episode of arrhythmia as a particular type of arrhythmia. In some examples, the report includes a subsection of the cardiac electrogram data obtained from patient 4 that coincides with the episode of arrhythmia. For example, computing system 24 may identify a subsection of the cardiac electrogram data of patient 4, wherein the subsection comprises cardiac electrogram data for a first time period prior to the episode of arrhythmia (e.g., typically less than 10 minutes prior to the onset of the episode of arrhythmia), a second time period during the occurrence of the episode of arrhythmia, and a third time period after the episode of arrhythmia (e.g., typically less than 10 minutes after the cessation of the episode of arrhythmia). As an example, a subsection of the cardiac electrogram data of patient 4 may be about 6 seconds in length and includes representative segments before, during, and after an episode of arrhythmia (if present in the cardiac electrogram data or waveform that is analyzed). In some examples, the episode duration differs by device type, and may further depend on a use case for the medical device, one or more settings of the medical device, or a particular type of arrhythmia sensed. For example, some types of arrhythmia self-terminate quickly, (resulting in a short duration episode), while other types of arrhythmia are sustained and of a length such that the recorded duration of the episode may depend on a designated memory space on the medical device. As an example, for atrial fibrillation (AF), the subsection of the cardiac electrogram data of patient 4 may include cardiac electrogram data during an onset time period, a segment of maximum AF likelihood, a segment of fastest AF rate, and an AF offset. Typically, a length of time of the cardiac electrogram data of the patient is greater than the first, second, and third time periods. Further, computing system 24 identifies one or more of the cardiac features that coincide with the first, second, and third time periods. Computing system 24 includes, in the report, the subsection of the cardiac electrogram data and the one or more of the cardiac features that coincide with the first, second, and third time periods.

In some examples, computing system 24 receives, from a clinician, one or more adjustments to an operation to the feature-based delineation of the cardiac electrogram data that are based on the report. Computing device 24 subsequently may perform feature-based delineation of the cardiac electrogram data of patient 4 in accordance with the one or more adjustments.

Figure 6:
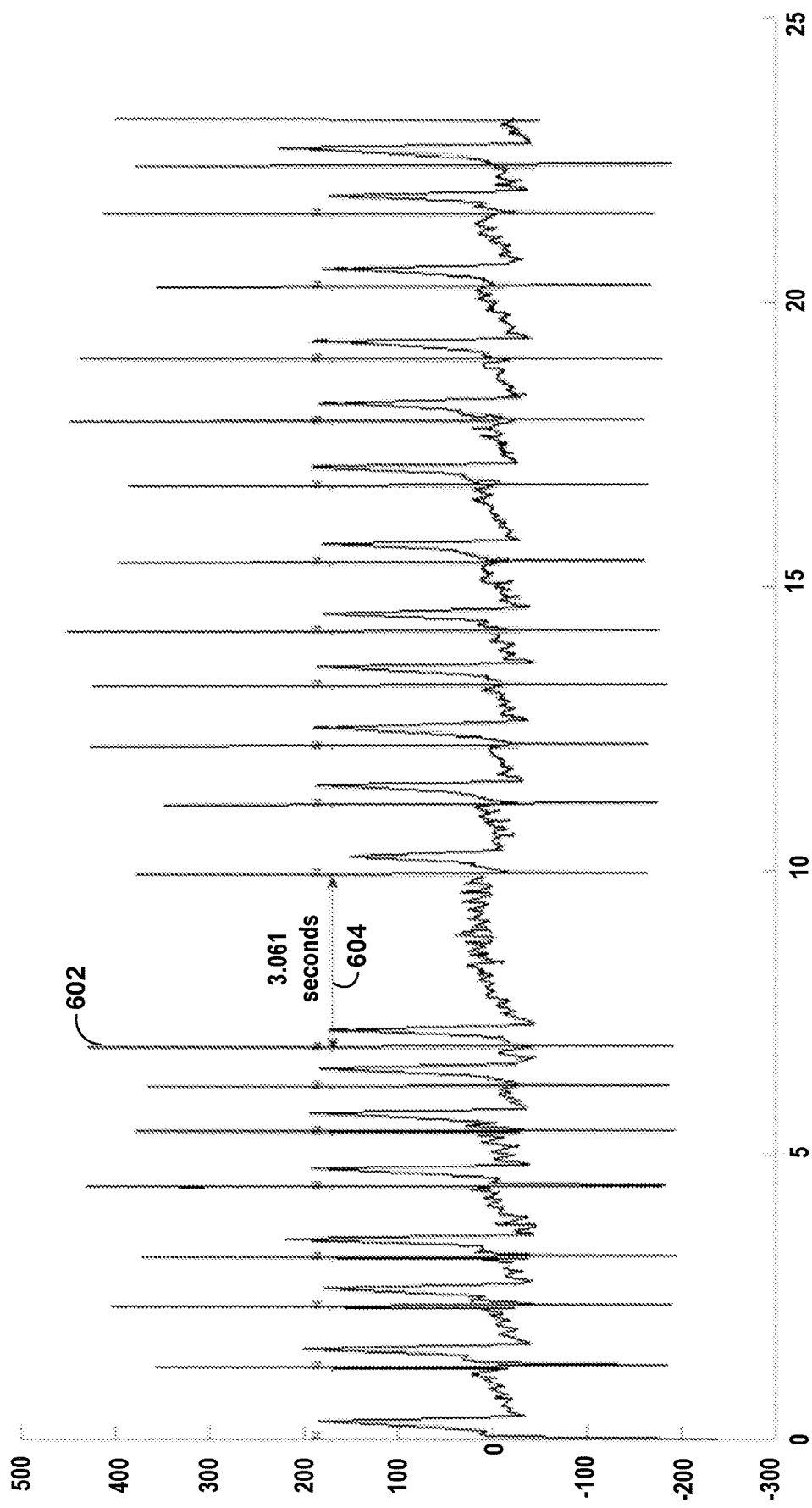
FIG. 6 is a chart illustrating an example electrocardiogram obtained from the patient of FIG. 1.

FIG. 6 is a chart illustrating example electrocardiogram 602 obtained from patient 4 of FIG. 1. Electrocardiogram 602 may be sensed, for example, by sensing circuitry 52 of IMD 10. Machine learning system 150 of FIG. 1 may apply a machine learning model to electrocardiogram 602 to determine that electrocardiogram 602 includes pause 604. Computing system 24 of FIG. 1 or IMD 10 of FIG. 1 (e.g., as part of IMD 10 initially detecting an arrhythmia) may perform feature delineation on electrocardiogram 602 to determine a length of pause 604. With respect to the example of FIG. 6, computing system 24 or IMD 10 determines, via feature delineation of electrocardiogram 602, that pause 604 has a length of 3.061 seconds. In one example, IMD 10 performs QRS detection from an on-device marker channel. The QRS flagging may be based on a conventional QRS algorithm. IMD 10 may use QRS markers to determine that the pause duration is 3.061 seconds.

Figure 7:
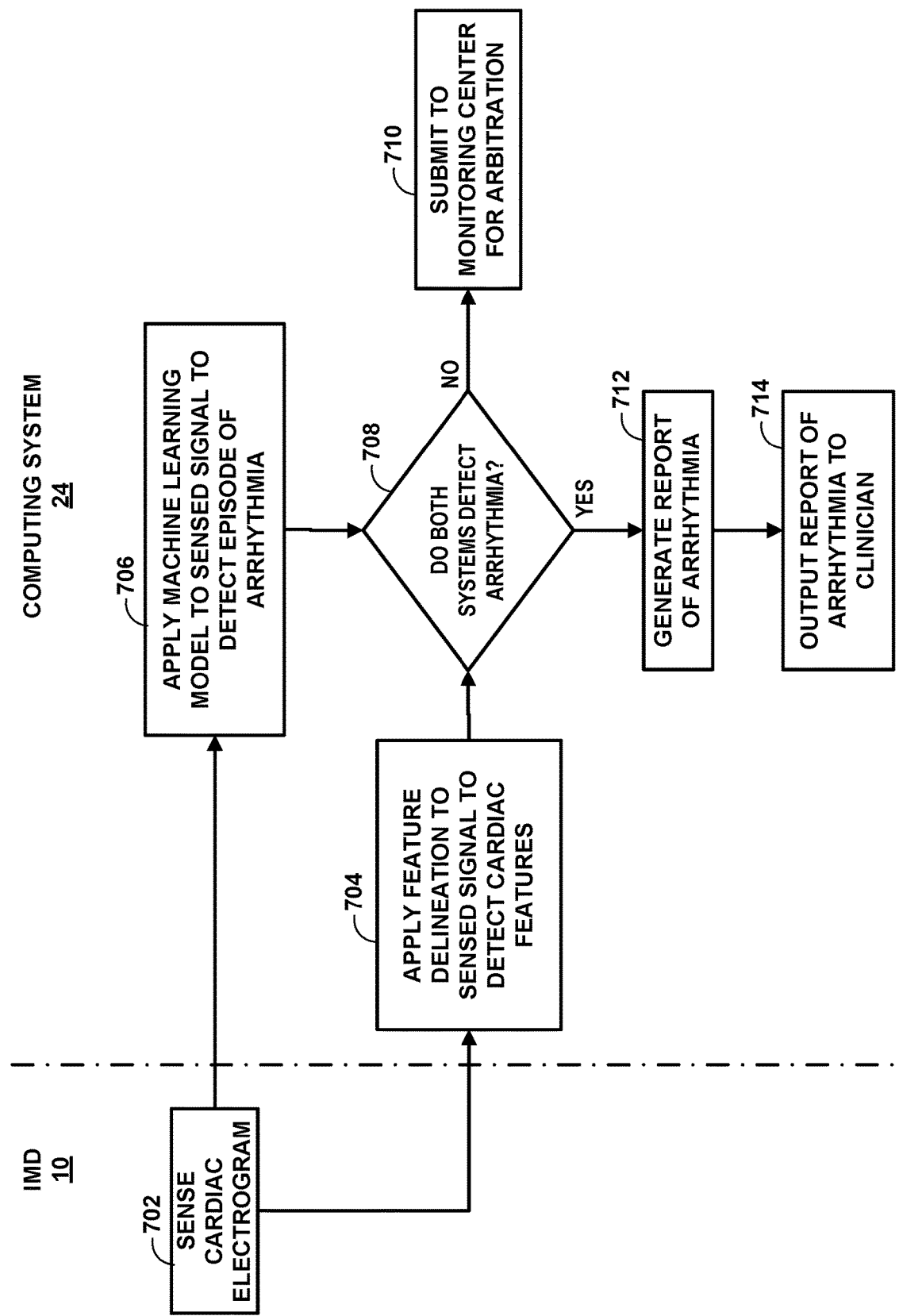
FIG. 7 is a flowchart illustrating an example operation in accordance with the techniques of the disclosure.

FIG. 7 is a flowchart illustrating an example operation in accordance with the techniques of the disclosure. For convenience, FIG. 7 is described with respect to FIG. 1. The operation of FIG. 7 is an operation for detecting and classifying cardiac arrhythmia in patient 4. Specifically, the operation of FIG. 7 depicts an implementation where computing system 24 uses machine learning arrhythmia detection of machine learning system 150 and feature delineation in parallel to perform cardiac arrhythmia detection, verification, and reporting.

As depicted in FIG. 7, IMD 10 senses cardiac electrogram data of patient 4 (702). Computing system 24 applies feature delineation to the cardiac electrogram data to detect one or more cardiac features (704). In the example of FIG. 7, computing system 24 performs feature delineation of the cardiac electrogram data. However, in other examples of the techniques of the disclosure, other devices, such as IMD 10, external device 12, or another external medical device, may perform feature delineation of the cardiac electrogram data. Machine learning system 150 of computing system 24 applies a machine learning model to the sensed cardiac electrogram to detect an episode of arrhythmia in patient 4 (706). The operation of steps 702, 704, and 706 may occur in a substantially similar fashion to steps 502, 504, and 506 of FIG. 5, respectively.

Computing system 24 determines whether both machine learning system 150 and the feature delineation operation of (704) detect an episode of cardiac arrhythmia (708). For example, computing system 24 may determine a level of confidence that the determination of arrhythmia by machine learning system 150 matches the determination of arrhythmia by the feature delineation operation of 704 (708). For example, if computing system 24 determines that both machine learning system 150 and the feature delineation operation of (704) detect an episode of cardiac arrhythmia (e.g., "YES" block of 708), then computing system 24 may generate a report of the arrhythmia (712) and outputs the report to a clinician or monitoring center (714). For example, computing system 24 populates a report with the detected arrhythmias along with the arrhythmia characteristics and outputs the report to the clinician. The operation of steps 712 and 714 may occur in a substantially similar fashion to steps 512 and 514 of FIG. 5, respectively.

As another example, if computing system 24 determines that machine learning system 150 and the feature delineation operation of (704) disagree as to whether an episode of cardiac arrhythmia is detected (e.g., "NO" block of 708), then computing system 24 submits the cardiac electrogram data to a monitoring center for arbitration (710). In other words, computing system 24 presents the cardiac electrogram data for human overview where there is a discrepancy between the two detection methods. Such a workflow may allow for the reduction in human review burden to only those arrhythmias that computing system 24 is unable to evaluate with a high degree of confidence. For example, if the arrhythmias detected via feature delineation are similar to arrhythmias independently detected by the machine learning model, then computing system 24 may determine that the arrhythmias detected via feature delineation are independently verified without requiring expert human review. Thus, the techniques of the disclosure may reduce the amount of review required by clinicians and/or experts, thereby reducing the administrative overhead and cost of cardiac monitoring of patient 4.

Figure 8:
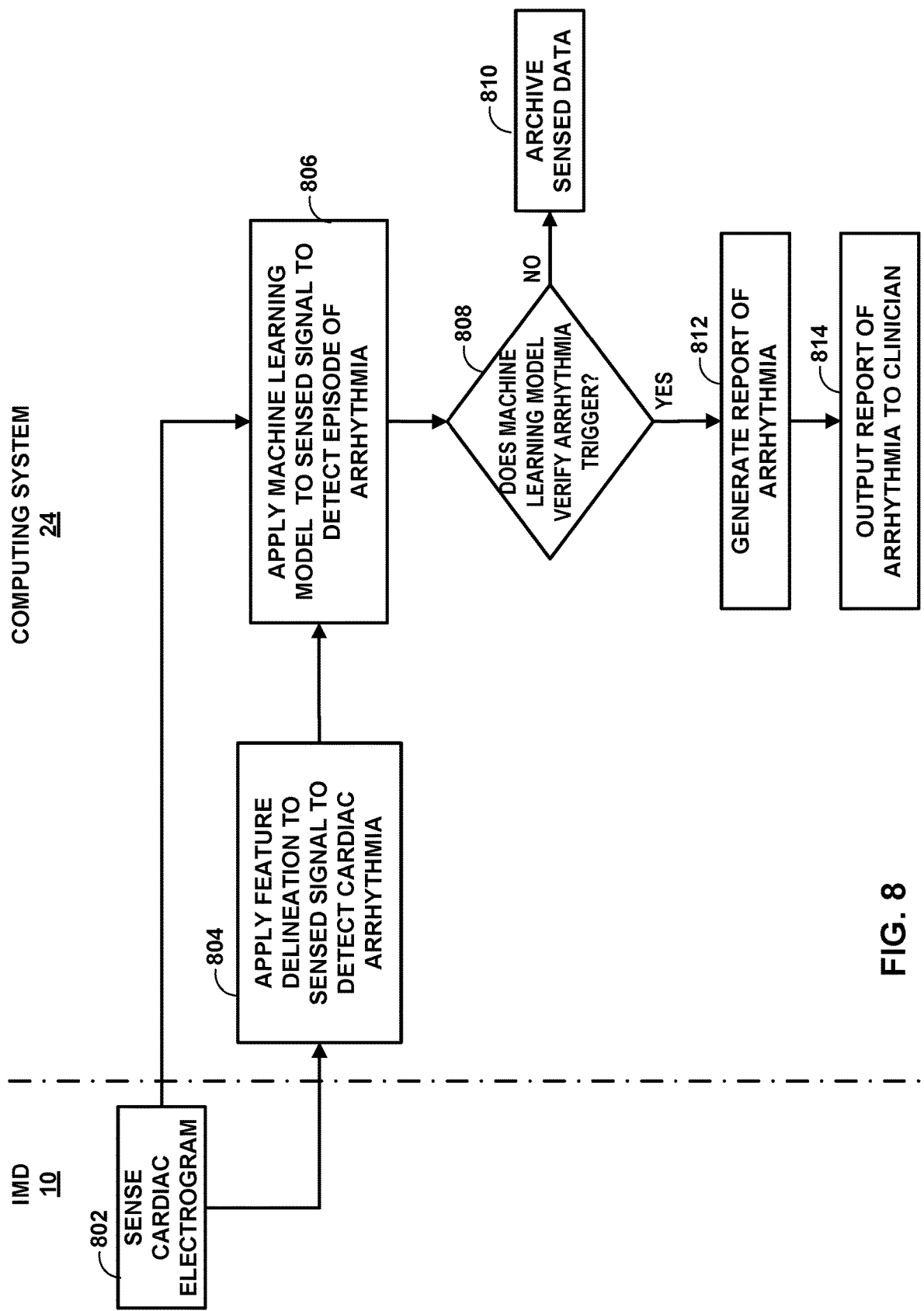
FIG. 8 is a flowchart illustrating an example operation in accordance with the techniques of the disclosure.

FIG. 8 is a flowchart illustrating an example operation in accordance with the techniques of the disclosure. For convenience, FIG. 8 is described with respect to FIG. 1. The operation of FIG. 8 is an operation for detecting and classifying cardiac arrhythmia in patient 4. Specifically, the operation of FIG. 8 depicts an implementation where computing system 24 uses feature delineation in series with machine learning arrhythmia detection of machine learning system 150 to perform cardiac arrhythmia detection, verification, and reporting.

As depicted in FIG. 8, IMD 10 senses cardiac electrogram data of patient 4 (802). The operation of step 802 may occur in a substantially similar fashion to step 502 of FIG. 5. Computing system 24 applies feature delineation to the cardiac electrogram data to detect a set of cardiac arrhythmias and one or more cardiac features (804). In some examples, computing system 24 applies feature delineation to detect arrhythmia such as bradycardia, tachycardia, pause, or atrial fibrillation based on rate and variability features in the cardiac electrogram data. In the example of FIG. 8, computing system 24 performs feature delineation as a screening step before delineating all arrhythmias (e.g., computing system 24 may use feature delineation to consider only tachyarrhythmia with heartrates greater than or equal to 120 BPM, bradyarrhythmia with heartrates less than or equal to 40 BPM, or arrhythmias with high RR variability). In other examples, such feature delineation may be implemented on low-power devices such as IMD 10 or other types of devices, such as external device 12 or another external medical device.

Upon detecting via feature delineation that an episode of cardiac arrhythmia has occurred in patient 4, machine learning system 150 of computing system 24 applies a machine learning model to the sensed cardiac electrogram to verify that the episode of arrhythmia has occurred (806). In some examples, machine learning system 150 applies the machine learning model to many different types of patient data, such as the cardiac electrogram data for patient 4, the trigger reason that caused feature delineation to detect an arrhythmia, one or more types of arrhythmias detected by feature delineation, or device characteristics of IMD 10 such as activity level, input impedance, battery level, etc.

In the example of FIG. 8, computing system 24 determines whether machine learning system 150 verifies the arrhythmia trigger of the feature delineation of step 804 (808). In other words, in response to determining that the feature delineation of step 804 has detected an episode of arrhythmia in patient 4, computing system 24 determines whether machine learning system 150 likewise detects an episode of arrhythmia in patient 4. The use of machine learning system 150 allows computing system 24 to verify whether the detection reason of the feature delineation of step 804 was appropriate (e.g., a bradycardia trigger of the feature delineation was truly indicative that an episode of bradycardia in patient 4 has occurred). The use of machine learning system 150 as a verification tool may assist computing system 24 in providing feedback to physicians for re-programming diagnostic devices for patient 4, such as IMD 10. Further, the use of machine learning system 150 as a verification tool may assist computing system 24 in automating the reporting of physiological parameters (e.g., report the device-detected AF burden as-is if all AF triggered episodes are appropriate, else, only consider the burden for appropriately-triggered episodes).

For example, if computing system 24 determines that machine learning system 150 verifies the detection of the episode of cardiac arrhythmia by the feature delineation operation of 804 (e.g., "YES" block of 808), then computing system 24 may generate a report of the arrhythmia (812) and outputs the report to a clinician or monitoring center (814). As another example, if computing system 24 determines that machine learning system 150 and the feature delineation operation of 804 disagree as to whether an episode of cardiac arrhythmia is detected (e.g., "NO" block of 808), then computing system 24 submits the cardiac electrogram data to a monitoring center for arbitration (810). The operation of steps 810, 812, and 814 may occur in a substantially similar fashion to steps 510, 512, and 514 of FIG. 5, respectively.

Figure 9:
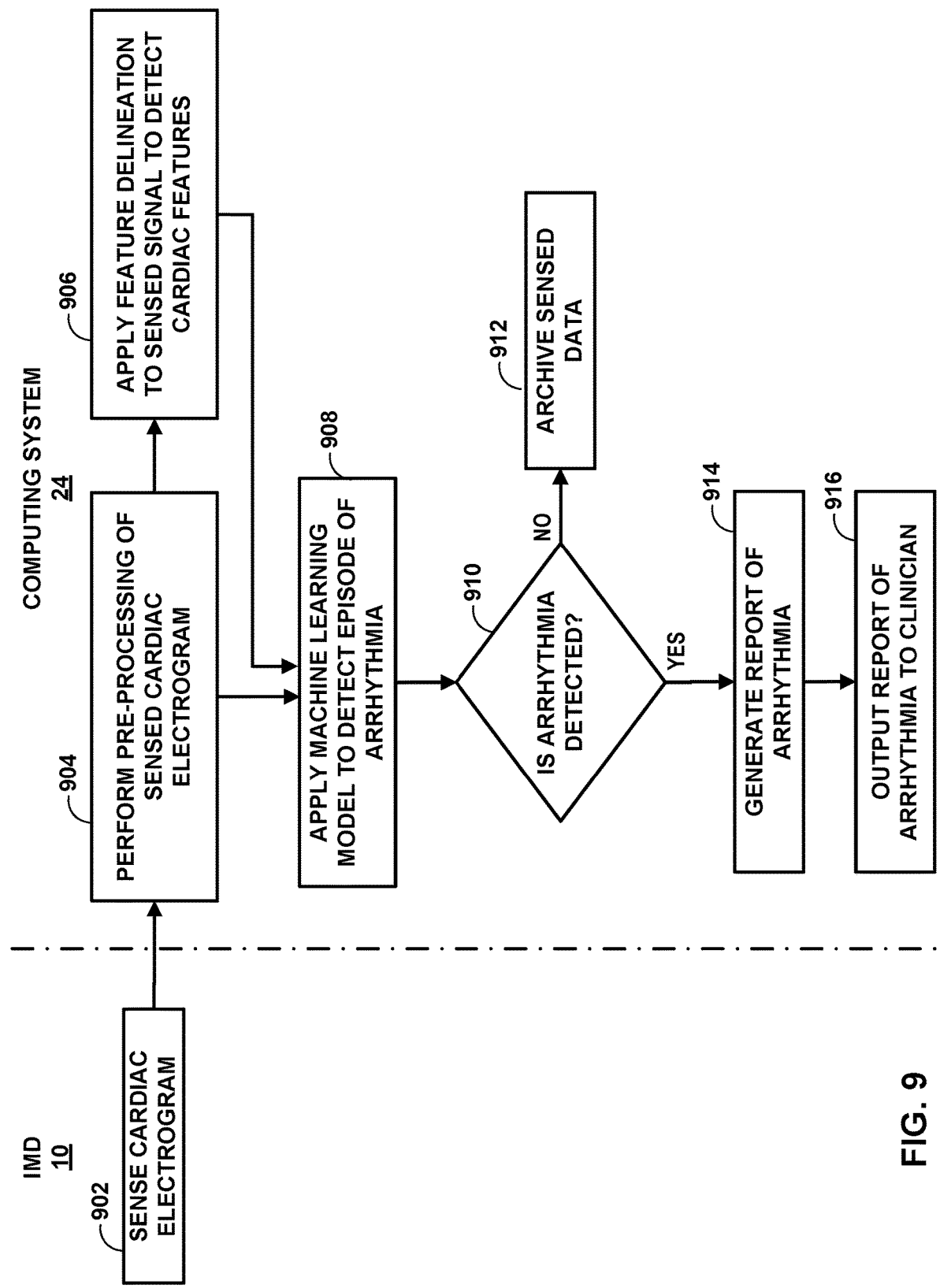
FIG. 9 is a flowchart illustrating an example operation in accordance with the techniques of the disclosure.

FIG. 9 is a flowchart illustrating an example operation in accordance with the techniques of the disclosure. For convenience, FIG. 9 is described with respect to FIG. 1. The operation of FIG. 9 is an operation for detecting and classifying cardiac arrhythmia in patient 4. Specifically, the operation of FIG. 9 depicts an implementation where computing system 24 preprocesses the cardiac electrogram data to generate an intermediate representation of the cardiac electrogram data, and applies machine learning system 150 to the intermediate representation of the cardiac electrogram data to perform cardiac arrhythmia detection, verification, and reporting.

In the example of FIG. 9, IMD 10 senses cardiac electrogram data of patient 4 (902). The operation of step 902 may occur in a substantially similar fashion to step 502 of FIG. 5. Computing system 24 performs pre-processing of the sensed cardiac electrogram data to generate an intermediate representation of the cardiac electrogram data (904). For example, computing system 24 performs QRS detection to detect a plurality of QRS windows within the sensed cardiac electrogram data. In one example, the window around the detected QRS includes data for 160 milliseconds prior to the detected QRS and data for 160 milliseconds after the detected QRS. In another example, the window around the detected QRS includes a data segment from a T-offset of a previous QRS to a T-offset of the current QRS. In some examples, computing system 24 may apply signal processing methods such as bandpass filtering or stationary wavelet decomposition that are used for QRS detection, flagging and delineation to the sensed cardiac electrogram data. For example, computing system 24 generates a wavelet decomposition of the cardiac electrogram of patient 4 for the window around the detected QRS.

Computing system 24 applies feature delineation to the intermediate representation of the cardiac electrogram data to detect one or more cardiac features (906). For example, computing system 24 applies feature delineation to the intermediate representation to detect and delineate a QRS segment (e.g., P-R intervals) of patient 4 from the window around the detected QRS, as well as a noise flag. In the example of FIG. 9, computing system 24 performs feature delineation of the cardiac electrogram data. However, in other examples of the techniques of the disclosure, other devices, such as IMD 10, external device 12, or another external medical device, may perform feature delineation of the cardiac electrogram data.

Machine learning system 150 of computing system 24 applies a machine learning model to the intermediate representation of the sensed cardiac electrogram to detect an episode of arrhythmia in patient 4 (908). For example, the machine learning model may receive, as an input, a plurality of cardiac electrogram segments, each segment including a window around a detected QRS, a QRS delineation for the segment, and a noise flag for the segment. Machine learning system 150 applies the machine learning model to the received segments to detect an episode of arrhythmia in patient 4.

In some examples, the machine learning model is tuned to capture segments of interest of each arrhythmia. For example, the machine learning model may process the sensed cardiac electrogram to capture an onset, an offset, a highest heartrate, and a lowest heartrate from the segment including the window around the detected QRS. In some examples, computing system 24 uses features derived from feature delineation such as QRS detection, such as the heartrate values of the cardiac electrogram segment, to characterize or contextualize a detection of arrhythmia by the machine learning model.

The use of signal decomposition to create the intermediate representation of the cardiac electrogram may allow for the use existing knowledge about the frequency bands of interest for arrhythmia detection. Further, the signal decomposition may limit the computational complexity of the machine learning model of machine learning system 150 such that the machine learning model may learn features for classification from only the cardiac electrogram subsegments corresponding to the detected QRS. Thus, such techniques may reduce the complexity of the machine learning model, allowing for a reduction in the size of the training set needed to generate the machine learning model as well as increasing the accuracy in the machine learning model.

In contrast to the operation of FIG. 5, computing system 24 may use the same signal pre-processing for both feature delineation detection of cardiac arrhythmia and/or cardiac features of step 906 and the machine learning model detection of cardiac arrhythmia. Furthermore, computing system 24 may use the QRS noise-flag and feature delineation as inputs for the machine learning model of machine learning system 150. The input cardiac electrogram complexes may be of the same duration (e.g., 320 milliseconds) or of different durations (e.g., the segment from the previous T-offset to the current T-offset).

Figure 10:
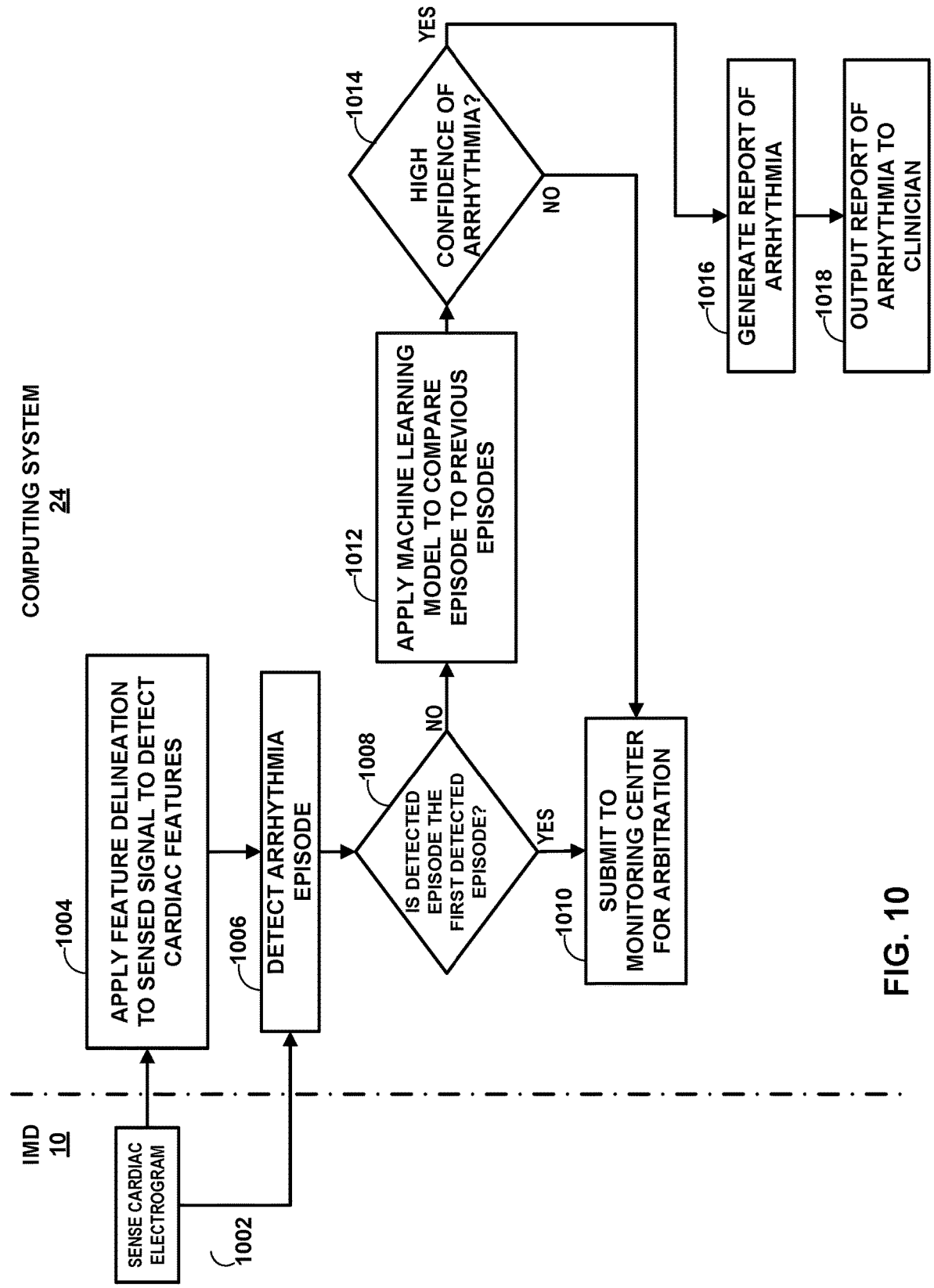
FIG. 10 is a flowchart illustrating an example operation in accordance with the techniques of the disclosure.

FIG. 10 is a flowchart illustrating an example operation in accordance with the techniques of the disclosure. For convenience, FIG. 10 is described with respect to FIG. 1. The operation of FIG. 10 is an operation for detecting and classifying cardiac arrhythmia in patient 4. Specifically, the operation of FIG. 10 depicts an implementation where computing system 24 uses feature delineation in series with machine learning arrhythmia detection of machine learning system 150 to build a dictionary of arrhythmias for use in cardiac arrhythmia detection, classification, and reporting.

The operation of FIG. 10 monitors cardiac electrogram data for patient 4, annotates detected arrhythmia, and reports such arrhythmia to a monitoring center. In some examples, the operation of FIG. 10 takes place within a centralized location such as the monitoring center. As another example, the operation of FIG. 10 may take place at a clinic on a patient-by-patient basis. As depicted in FIG. 10, IMD 10 senses cardiac electrogram data of patient 4 (1002). Computing system 24 further applies feature delineation to the cardiac electrogram data to detect one or more cardiac features (1004). The operation of steps 1002 and 1004 may occur in a substantially similar fashion to steps 502 and 504 of FIG. 5, respectively.

Computing system 24 further applies feature delineation to the cardiac electrogram data to detect one or more episodes of arrhythmia (1006). In some examples, the feature delineation causes a cardiac electrogram auto-trigger. In the example of FIG. 10, computing system 24 performs the feature delineation. However, in other examples, the arrhythmia detection and cardiac electrogram episode autotrigger may occur on another device, such as IMB 10, external device 12, or another external medical device, or via post-processing in Holter-like systems.

If an episode of arrhythmia has been triggered from a specific patient for the first time, computing system 24 presents the episode for arrhythmia review such that the episode may be used as a reference episode in a patient-specific "episode dictionary." For example, in response to detecting an episode of arrhythmia, computing system 24 determines whether the episode of arrhythmia is the first detected episode. If the episode of arrhythmia is the first detected episode (e.g., "YES" block of 1008), computing system 24 generates a report of the episode of arrhythmia and submits the report to a monitoring center or clinician for evaluation (1010). For example, if an episode is a first AF-trigger, the episode is presented for monitoring center review. As another example, if an episode is a first AF trigger that occurs at night, the episode is presented for monitoring center review. In one example, the report includes an indication that the episode of arrhythmia has occurred in the patient and one or more of the cardiac features that coincide with the episode of arrhythmia. Computing system 24 receives, from the monitoring center, an indication verifying whether the cardiac features included in the report are indicative of an episode of arrhythmia. In an example where the cardiac features are indicative of an episode of arrhythmia, computing system 24 further receives a classification of the type of arrhythmia indicated by the cardiac features included in the report. Computing system 24 may store the indication of the classification of the type of arrhythmia together with the cardiac features in a database so as to build a "dictionary" of cardiac arrhythmia.

In some examples, computing system 24 may detect multiple episodes of arrhythmia that have similar arrhythmia content, annotations, and/or cardiac features. For example, with respect to atrial fibrillation (AF) monitoring, most episode triggers have AF. Another example is where feature delineation may generate several false triggers of arrhythmia, due to patient-specific reasons such as signal acquisition location and orientation (e.g., PACs with low-amplitude P-waves). For example, computing system 24 may input any subsequently detected episode to a machine learning model (with other episode characteristics such as trigger reason, activity level, and time of day). The machine learning model of machine learning system 150 compares features of the episode to features of episodes in the "episode dictionary" of patient 4. If the machine learning model determines that a similar episode is present in the dictionary with a high degree of confidence, then the original monitoring center annotations are used as-is for reporting the episode. If no similar episode is identified, then computing system 24 may determine that the episode characteristics are different and therefore present the episode for monitoring center review and reporting. Thus, the operation of FIG. 10 may increase the efficiency of arrhythmia annotation by minimizing redundant annotations in arrhythmia episodes that have similar characteristics so as to reduce the volume of arrhythmia episodes that require monitoring center review.

The techniques of the disclosure may provide the further advantage that the machine learning model of machine learning system 150 need not be tuned to detect a wide variety of arrhythmias. Instead, the machine learning model may be tuned only to accurately identify a new episode as similar or dissimilar to a previous episode. For example, if there is similarity between two episodes of arrhythmia, then computing system 24 may apply the previous, patient-specific findings to the new episode as well. If there is dissimilarity, then computing system 24 may request a human expert to make a determination of whether the episode is an episode of arrhythmia, and/or the type of arrhythmia presented by the episode. Accordingly, the machine learning model is not required to identify specific arrhythmias with a high level of confidence. The machine learning model needs only to be accurate in identifying differences between two episodes of arrhythmia in order to accurately present episodes with different cardiac features (e.g., novel or unclassified rhythm content) for human review. Thus, the techniques of the disclosure may allow computing system 24 to detect episodes of arrhythmia that machine learning model 150 has not been specifically trained to detect. Furthermore, the techniques of the disclosure may reduce the complexity of the machine learning model while retaining high accuracy in arrhythmia detection and classification.

For example, with respect to the operation of FIG. 10, if the episode of arrhythmia is not the first detected episode (e.g., "NO" block of 1008), machine learning system 150 applies a machine learning model to the detected cardiac features to compare the cardiac features to other cardiac features of previous episodes of arrhythmia (1012). For example, machine learning system 150 may apply the machine learning model to the detected cardiac features to determine whether the cardiac features match other cardiac features of previous episodes of arrhythmia and an estimate of a confidence level or certainty in the comparison. In some examples, computing system 24 resets the similarity comparison after a certain duration (e.g., every day) or upon demand (e.g., when patient medication changes occur). This may ensure that some episodes of arrhythmia are reviewed by the monitoring center or clinician intermittently to ensure that new or changing arrhythmias are not missed.

In response to determining that the machine learning model does not have a high confidence level or certainty in the comparison (e.g., "NO" block of 1014), computing system 24 generates a report of the episode of arrhythmia and submits the report to a monitoring center or clinician for evaluation (1010). Computing system 24 receives an indication verifying that the cardiac features included in the report are indicative of an episode of arrhythmia and a classification of the type of arrhythmia, and store the indication of the classification of the type of arrhythmia together with the cardiac features in the database so as to update the dictionary of cardiac arrhythmia with the detected cardiac features and a classification of arrhythmia indicated by the detected cardiac features.

In response to determining that the machine learning model does have a high confidence level or certainty in the comparison (e.g., "YES" block of 1014), computing system 24 may determine that the cardiac features are indicative of the type of a previous episode of arrhythmia. Computing system 24 generates a report of the arrhythmia (1016) and outputs the report to the monitoring center (1018). The operation of steps 1016 and 1018 may occur in a substantially similar fashion to steps 512 and 514 of FIG. 5, respectively.

The following examples may illustrate one or more aspects of the disclosure.

Example 1. A method comprising: receiving, by a computing device comprising processing circuitry and a storage medium, cardiac electrogram data of a patient sensed by a medical device; applying, by the computing device, a machine learning model, trained using cardiac electrogram data for a plurality of patients, to the received cardiac electrogram data to determine, based on the machine learning model, that an episode of arrhythmia has occurred in the patient; performing, by the computing device, feature-based delineation of the received cardiac electrogram data to obtain cardiac features present in the cardiac electrogram data; in response to determining that the episode of arrhythmia has occurred in the patient: generating, by the computing device, a report comprising an indication that the episode of arrhythmia has occurred in the patient and one or more of the cardiac features that coincide with the episode of arrhythmia; and outputting, by the computing device and for display, the report comprising the indication that the episode of arrhythmia has occurred in the patient and the one or more of the cardiac features that coincide with the episode of arrhythmia.

Example 2. The method of example 1, wherein performing feature-based delineation of the cardiac electrogram data to obtain the cardiac features present in the cardiac electrogram data comprises performing at least one of QRS detection, refractory processing, noise processing, or delineation of the cardiac electrogram data to obtain cardiac features present in the cardiac electrogram data.

Example 3. The method of any of examples 1 or 2, wherein applying the machine learning model to determine that the episode of arrhythmia has occurred in the patient comprises applying the machine learning model to determine that an episode of at least one of bradycardia, tachycardia, atrial fibrillation, ventricular fibrillation, or AV Block has occurred in the patient.

Example 4. The method of any of examples 1 through 3, wherein the cardiac features present in the cardiac electrogram data are one or more of a mean heartrate of the patient, a minimum heartrate of the patient, a maximum heartrate of the patient, a PR interval of a heart of the patient, a variability of heartrate of the patient, one or more amplitudes of one or more features of an electrocardiogram (ECG) of the patient, or an interval between the or more features of the ECG of the patient.

Example 5. The method of any of examples 1 through 4, wherein the machine learning model trained using cardiac electrogram data for the plurality of patients comprises a machine learning model trained using a plurality of electrocardiogram (ECG) waveforms, each ECG waveform labeled with one or more episodes of arrhythmia of one or more types in a patient of the plurality of patients.

Example 6. The method of any of examples 1 through 5, wherein applying the machine learning model to the received cardiac electrogram data further comprises applying the machine learning model to at least one of: one or more characteristics of the received cardiac electrogram data correlated to arrhythmia in the patient; an activity level of the medical device; an input impedance of the medical device; or a battery level of the medical device.

Example 7. The method of any of examples 1 through 6, wherein the method further comprises, in response to outputting the report comprising the indication that the episode of arrhythmia has occurred in the patient and the one or more of the cardiac features that coincide with the episode of arrhythmia: receiving, by the computing device and from a user, an adjustment to the feature-based delineation of the cardiac electrogram data; and performing, in accordance with the adjustment, feature-based delineation of the cardiac electrogram data to obtain second cardiac features present in the cardiac electrogram data.

Example 8. The method of any of examples 1 through 7, wherein the cardiac electrogram data of the patient comprises an electrocardiogram (ECG) of the patient, and wherein generating the report comprising the indication that the episode of arrhythmia has occurred in the patient and the one or more of the cardiac features that coincide with the episode of arrhythmia comprises: identifying a subsection of the ECG of the patient, wherein the subsection comprises ECG data for a first time period prior to the episode of arrhythmia, a second time period during the episode of arrhythmia, and a third time period after the episode of arrhythmia, and wherein a length of time of the ECG of the patient is greater than the first, second, and third time periods; identifying one or more of the cardiac features that coincide with the first, second, and third time periods; and including, in the report, the subsection of the ECG and the one or more of the cardiac features that coincide with the first, second, and third time periods.

Example 9. The method of any of examples 1 through 8, wherein the method further comprises processing, by the computing device, the received cardiac electrogram data to generate an intermediate representation of the received cardiac electrogram data, wherein applying the machine learning model, trained using cardiac electrogram data for the plurality of patients, to the received cardiac electrogram data to determine that the episode of arrhythmia has occurred in the patient comprises applying a machine learning model, trained using intermediate representations of cardiac electrogram data for a plurality of patients, to the intermediate representation of the received cardiac electrogram data and the cardiac features present in the cardiac electrogram data to determine, based on the machine learning model, that the episode of arrhythmia has occurred in the patient.

Example 10. The method of example 9, wherein processing the received cardiac electrogram data to generate the intermediate representation of the received cardiac electrogram data comprises at least one of: applying a filter to the received cardiac electrogram data; performing signal decomposition on the received cardiac electrogram data.

Example 11. The method of example 10, wherein performing signal decomposition on the received cardiac electrogram data comprises performing wavelet decomposition on the received cardiac electrogram data.

Example 12. A method comprising: receiving, by a computing device comprising processing circuitry and a storage medium, cardiac electrogram data of a patient sensed by a medical device; obtaining, by the computing device, a first classification of arrhythmia in the patient determined by feature-based delineation of the received cardiac electrogram data, wherein the feature-based delineation identifies cardiac features present in the cardiac electrogram data; applying, by the computing device, a machine learning model, trained using cardiac electrogram data for a plurality of patients, to the received cardiac electrogram data to determine, based on the machine learning model, a second classification of arrhythmia in the patient; determining, by the computing device and based on the first classification and second classification, that an episode of arrhythmia has occurred in the patient; and in response to determining that the episode of arrhythmia has occurred in the patient: generating, by the computing device, a report comprising an indication that the episode of arrhythmia has occurred in the patient and one or more of the cardiac features that coincide with the episode of arrhythmia; and outputting, by the computing device and for display, the report comprising the indication that the episode of arrhythmia has occurred in the patient and the one or more of the cardiac features that coincide with the episode of arrhythmia.

Example 13. The method of example 12, wherein determining, based on the first classification and second classification, that the episode of arrhythmia has occurred in the patient comprises: determining, by the computing device, a degree of similarity of the first classification and the second classification; and based on the degree of similarity of the first classification and the second classification, determining, by the computing device, that the episode of arrhythmia has occurred in the patient.

Example 14. The method of example 12, wherein applying the machine learning model to the received cardiac electrogram data to determine the second classification of arrhythmia in the patient comprises applying the machine learning model to the received cardiac electrogram data and the cardiac features identified by the feature-based delineation of the received cardiac electrogram data to determine the second classification of arrhythmia in the patient; and wherein determining, based on the first classification and second classification, that the episode of arrhythmia has occurred in the patient comprises: determining that the first classification is indicative that the episode of arrhythmia has occurred in the patient; and in response determining that the first classification is indicative that the episode of arrhythmia has occurred in the patient, determining that the second classification verifies that the episode of arrhythmia has occurred in the patient; and in response to determining that the second classification verifies that the episode of arrhythmia has occurred in the patient, determining that the episode of arrhythmia has occurred in the patient.

Example 15. The method of any of examples 12 through 14, wherein obtaining, by the computing device, the first classification of arrhythmia in the patient determined by feature-based delineation of the received cardiac electrogram data comprises performing, by the computing device, feature-based delineation of the received cardiac electrogram data to determine the first classification of arrhythmia in the patient.

Example 16. The method of any of examples 12 through 15, wherein obtaining, by the computing device, the first classification of arrhythmia in the patient determined by feature-based delineation of the received cardiac electrogram data comprises receiving, by the computing device and from the medical device, the first classification of arrhythmia in the patient determined by feature-based delineation by the medical device of the received cardiac electrogram data.

Example 17. The method of any of examples 12 through 16, wherein obtaining the first classification of arrhythmia in the patient determined by feature-based delineation of the received cardiac electrogram data comprises obtaining the first classification of arrhythmia in the patient determined by at least one of QRS detection, refractory processing, noise processing, or delineation of the cardiac electrogram data to obtain cardiac features present in the cardiac electrogram data.

Example 18. The method of any of examples 12 through 17, wherein applying the machine learning model to determine the second classification of arrhythmia in the patient comprises applying the machine learning model to determine that an episode of at least one of bradycardia, tachycardia, atrial fibrillation, ventricular fibrillation, or AV Block has occurred in the patient.

Example 19. The method of any of examples 12 through 18, wherein the cardiac features present in the cardiac electrogram data are one or more of a mean heartrate of the patient, a minimum heartrate of the patient, a maximum heartrate of the patient, a PR interval of a heart of the patient, a variability of heartrate of the patient, one or more amplitudes of one or more features of an electrocardiogram (ECG) of the patient, or an interval between the or more features of the ECG of the patient.

Example 20. The method of any of examples 12 through 19, wherein the machine learning model trained using cardiac electrogram data for the plurality of patients comprises a machine learning model trained using a plurality of electrocardiogram (ECG) waveforms, each ECG waveform labeled with one or more episodes of arrhythmia of one or more types in a patient of the plurality of patients.

Example 21. The method of any of examples 12 through 20, wherein applying the machine learning model to the received cardiac electrogram data further comprises applying the machine learning model to at least one of: one or more characteristics of the received cardiac electrogram data correlated to arrhythmia in the patient; an activity level of the medical device; an input impedance of the medical device; or a battery level of the medical device.

Example 22. The method of any of examples 12 through 21, wherein the cardiac electrogram data of the patient comprises an electrocardiogram (ECG) of the patient, and wherein generating the report comprising the indication that the episode of arrhythmia has occurred in the patient and the one or more of the cardiac features that coincide with the episode of arrhythmia comprises: identifying a subsection of the ECG of the patient, wherein the subsection comprises ECG data for a first time period prior to the episode of arrhythmia, a second time period during the episode of arrhythmia, and a third time period after the episode of arrhythmia, and wherein a length of time of the ECG of the patient is greater than the first, second, and third time periods; identifying one or more of the cardiac features that coincide with the first, second, and third time periods; and including, in the report, the subsection of the ECG and the one or more of the cardiac features that coincide with the first, second, and third time periods.

Example 23. A method comprising: receiving, by a computing device comprising processing circuitry and a storage medium, cardiac electrogram data of a patient sensed by a medical device; obtaining, by the computing device, a first classification of arrhythmia in the patient determined by feature-based delineation of the received cardiac electrogram data, wherein the feature-based delineation identifies first cardiac features present in the cardiac electrogram data that coincide with the first classification of arrhythmia in the patient; determining, by the computing device, that one or more episodes of arrhythmia of the first classification have previously occurred in the patient; in response to determining that the one or more episodes of arrhythmia of the first classification have previously occurred in the patient, applying, by the computing device, a machine learning model, trained using cardiac electrogram data for a plurality of patients, to the received cardiac electrogram data and the first cardiac features present in the cardiac electrogram data to determine, based on the machine learning model, that the first cardiac features are similar to cardiac features that coincide with the one or more episodes of arrhythmia of the first classification that have previously occurred in the patient; in response to determining that the first cardiac features are similar to the cardiac features that coincide with the one or more episodes of arrhythmia of the first classification that have previously occurred in the patient, determining, by the computing device, that an episode of arrhythmia of the first classification has occurred in the patient; and in response to determining that that the episode of arrhythmia of the first classification has occurred in the patient:

generating, by the computing device, a report comprising an indication that the episode of arrhythmia of the first classification has occurred in the patient and one or more of the cardiac features that coincide with the episode of arrhythmia; and outputting, by the computing device and for display, the report comprising the indication that the episode of arrhythmia has occurred in the patient and the one or more of the cardiac features that coincide with the episode of arrhythmia.

Example 24. The method of example 23, further comprising: obtaining, by the computing device, a second classification of arrhythmia in the patient determined by feature-based delineation of the received cardiac electrogram data, wherein the feature-based delineation identifies second cardiac features present in the cardiac electrogram data that coincide with the second classification of arrhythmia in the patient; determining, by the computing device, that one or more episodes of arrhythmia of the second classification have not previously occurred in the patient; in response to determining that the one or more episodes of arrhythmia of the second classification have not previously occurred in the patient: outputting, by the computing device and for display, the second cardiac features and at least a portion of the received cardiac electrogram data; receiving, by the computing device and from a user, an indication that the second cardiac features demonstrate an episode of arrhythmia of the second classification in the patient; and storing, by the computing device, the indication that the second cardiac features demonstrate the episode of arrhythmia of the second classification in the patient and the second cardiac features.

Example 25. The method of example 24, further comprising: obtaining, by the computing device, a second classification of arrhythmia in the patient determined by feature-based delineation of the received cardiac electrogram data, wherein the feature-based delineation identifies third cardiac features present in the cardiac electrogram data that coincide with the second classification of arrhythmia in the patient; determining, by the computing device, that one or more episodes of arrhythmia of the second classification have previously occurred in the patient; in response to determining that the one or more episodes of arrhythmia of the second classification have previously occurred in the patient, applying, by the computing device, the machine learning model to the received cardiac electrogram data and the third cardiac features present in the cardiac electrogram data to determine, based on the machine learning model, that the third cardiac features are similar to the second cardiac features that coincide with the one or more episodes of arrhythmia of the second classification that have previously occurred in the patient; in response to determining that the third cardiac features are similar to the second cardiac features that coincide with the one or more episodes of arrhythmia of the second classification that have previously occurred in the patient, determining, by the computing device, that an episode of arrhythmia of the second classification has occurred in the patient; and in response to determining that that the third episode of arrhythmia has occurred in the patient: generating, by the computing device, a second report comprising an indication that the episode of arrhythmia of the third classification has occurred in the patient and one or more of the third cardiac features that coincide with the episode of arrhythmia of the third classification; and outputting, by the computing device and for display, the report comprising the indication that the episode of arrhythmia of the third classification has occurred in the patient and the one or more of the third cardiac features that coincide with the episode of arrhythmia of the third classification.

Example 26. The method of any of examples 23 through 25, wherein applying the machine learning model to the received cardiac electrogram data and the first cardiac features present in the cardiac electrogram data to determine, based on the machine learning model, that the first cardiac features are similar to the cardiac features that coincide with the one or more episodes of arrhythmia of the first classification that have previously occurred in the patient comprises: applying the machine learning model to the first cardiac features to output: a preliminary determination that the first cardiac features are similar to the cardiac features that coincide with the one or more episodes of arrhythmia of the first classification that have previously occurred in the patient; and an estimate of certainty in the preliminary determination; and in response to determining that the estimate of certainty in the preliminary determination is greater than a predetermined threshold, determining that the first cardiac features are similar to the cardiac features that coincide with the one or more episodes of arrhythmia of the first classification that have previously occurred in the patient.

Example 27. The method of any of examples 23 through 26, wherein performing feature-based delineation of the cardiac electrogram data to obtain the cardiac features present in the cardiac electrogram data comprises performing at least one of QRS detection, refractory processing, noise processing, or delineation of the cardiac electrogram data to obtain cardiac features present in the cardiac electrogram data.

Example 28. The method of any of examples 23 through 27, wherein applying the machine learning model to determine that the first cardiac features are similar to cardiac features that coincide with the one or more episodes of arrhythmia of the first classification that have previously occurred in the patient comprises applying the machine learning model to determine that the first cardiac features are indicative of an episode of at least one of bradycardia, tachycardia, atrial fibrillation, ventricular fibrillation, or AV Block that has previously occurred in the patient.

Example 29. The method of any of examples 23 through 28, wherein the first cardiac features present in the cardiac electrogram data are one or more of a mean heartrate of the patient, a minimum heartrate of the patient, a maximum heartrate of the patient, a PR interval of a heart of the patient, a variability of heartrate of the patient, one or more amplitudes of one or more features of an electrocardiogram (ECG) of the patient, or an interval between the or more features of the ECG of the patient.

Example 30. The method of any of examples 23 through 29, wherein the machine learning model trained using cardiac electrogram data for the plurality of patients comprises a machine learning model trained using a plurality of electrocardiogram (ECG) waveforms, each ECG waveform labeled with one or more episodes of arrhythmia of one or more types in a patient of the plurality of patients.

Example 31. The method of any of examples 23 through 30, wherein applying the machine learning model to the received cardiac electrogram data further comprises applying the machine learning model to at least one of: one or more characteristics of the received cardiac electrogram data correlated to arrhythmia in the patient; an activity level of the medical device; an input impedance of the medical device; or a battery level of the medical device.

Example 32. The method of any of examples 23 through 31, wherein the method further comprises, in response to outputting the report comprising the indication that the episode of arrhythmia has occurred in the patient and the one or more of the cardiac features that coincide with the episode of arrhythmia: receiving, by the computing device and from a user, an adjustment to the feature-based delineation of the cardiac electrogram data; and performing, in accordance with the adjustment, feature-based delineation of the cardiac electrogram data to obtain second cardiac features present in the cardiac electrogram data.

Example 33. The method of any of examples 23 through 32, wherein the cardiac electrogram data of the patient comprises an electrocardiogram (ECG) of the patient, and wherein generating the report comprising the indication that the episode of arrhythmia has occurred in the patient and the one or more of the cardiac features that coincide with the episode of arrhythmia comprises: identifying a subsection of the ECG of the patient, wherein the subsection comprises ECG data for a first time period prior to the episode of arrhythmia, a second time period during the episode of arrhythmia, and a third time period after the episode of arrhythmia, and wherein a length of time of the ECG of the patient is greater than the first, second, and third time periods; identifying one or more of the first cardiac features that coincide with the first, second, and third time periods; and including, in the report, the subsection of the ECG and the one or more of the first cardiac features that coincide with the first, second, and third time periods.

Example 34. The method of any of examples 23 through 33, wherein the method further comprises processing, by the computing device, the received cardiac electrogram data to generate an intermediate representation of the received cardiac electrogram data, wherein applying the machine learning model, trained using cardiac electrogram data for the plurality of patients, to the received cardiac electrogram data to determine that the episode of arrhythmia has occurred in the patient comprises applying a machine learning model, trained using intermediate representations of cardiac electrogram data for a plurality of patients, to the intermediate representation of the received cardiac electrogram data and the cardiac features present in the cardiac electrogram data to determine, based on the machine learning model, that a similar episode of arrhythmia has occurred in the patient.

Example 35. The method of example 34, wherein processing the received cardiac electrogram data to generate an intermediate representation of the received cardiac electrogram data comprises at least one of: applying a filter to the received cardiac electrogram data; performing signal decomposition on the received cardiac electrogram data.

Example 36. The method of example 35, wherein performing signal decomposition on the received cardiac electrogram data comprises performing wavelet decomposition on the received cardiac electrogram data.

In some examples, the techniques of the disclosure include a system that comprises means to perform any method described herein. In some examples, the techniques of the disclosure include a computer-readable medium comprising instructions that cause processing circuitry to perform any method described herein.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module, unit, or circuit for purposes of clarity, it should be understood that the techniques of this disclosure may be performed by a combination of units, modules, or circuitry associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing circuitry" as used herein may refer to any of the foregoing structure or any other physical structure suitable for implementation of the described techniques. Also, the techniques could be fully implemented in one or more circuits or logic elements.

Various examples have been described. These and other examples are within the scope of the following claims.

What is claimed is:

1. A device comprising processing circuitry and a storage medium, wherein the processing circuitry is configured to:
apply a machine learning model, trained using electrocardiogram (ECG) data for a plurality of patients, to sensed ECG data of a patient to determine, based on the machine learning model, that an episode of arrhythmia has occurred in the patient;
perform feature-based delineation of the sensed ECG data to obtain cardiac features present in the sensed ECG data; and
in response to determining that the episode of arrhythmia has occurred in the patient, generate data comprising an indication that the episode of arrhythmia has occurred in the patient and one or more of the cardiac features that coincide with the episode of arrhythmia.

2. The device of claim 1, wherein, to perform feature-based delineation, the processing circuitry is configured to perform QRS detection.

3. The device of claim 1, wherein the cardiac features present in the sensed ECG data comprise one or more of a mean heartrate of the patient, a minimum heartrate of the patient, a maximum heartrate of the patient, a variability of heartrate of the patient, one or more amplitudes of one or more features of the sensed ECG of the patient, or an interval between the or more features of the ECG of the patient.

4. The device of claim 1, wherein the processing circuitry is configured to apply the machine learning model to the sensed ECG data of the patient to determine, based on the machine learning model, that that an episode of at least one of bradycardia, tachycardia, or atrial fibrillation has occurred in the patient.

5. The device of claim 1, wherein the processing circuitry is further configured to:
receive an adjustment to the feature-based delineation of the ECG data in response to the data comprising the indication that the episode of arrhythmia has occurred in the patient and one or more of the cardiac features that coincide with the episode of arrhythmia; and
perform, in accordance with the adjustment, feature-based delineation of the ECG data to obtain second cardiac features present in the ECG data.

6. The device of claim 1, wherein, to generate the data comprising the indication that the episode of arrhythmia has occurred in the patient and one or more of the cardiac features that coincide with the episode of arrhythmia, the processing circuitry is configured to:
identify a subsection of the ECG of the patient, wherein the subsection comprises ECG data for a first time period prior to the episode of arrhythmia, a second time period during the episode of arrhythmia, and a third time period after the episode of arrhythmia, and wherein a length of time of the ECG of the patient is greater than the first, second, and third time periods;
identify one or more of the cardiac features that coincide with the first, second, and third time periods; and
include, in the data, the subsection of the ECG and the one or more of the cardiac features that coincide with the first, second, and third time periods.

7. The device of claim 1, wherein the processing circuitry is configured to:
process the sensed ECG data to generate an intermediate representation of the sensed ECG data; and
to apply the machine learning model, apply a machine learning model, trained using intermediate representations of ECG data for a plurality of patients, to the intermediate representation of the sensed ECG data and the cardiac features present in the sensed ECG data to determine, based on the machine learning model, that the episode of arrhythmia has occurred in the patient.

8. The device of claim 1, wherein the processing circuitry is configured to:
determine a first classification of arrhythmia in the patient based on the feature-based delineation of the sensed ECG data;
determine a second classification of arrhythmia based on the application of the machine learning model to the sensed ECG data; and
determine that the episode of arrhythmia occurred in the patient based on the first classification and second classification.

9. The device of claim 8, wherein, to determine that the episode of arrhythmia has occurred in the patient based on the first classification and second classification, the processing circuitry is configured to:
determine a degree of similarity of the first classification and the second classification; and
based on the degree of similarity of the first classification and the second classification, determine that the episode of arrhythmia has occurred in the patient.

10. The device of claim 8, wherein, to apply the machine learning model to the sensed ECG data, the processing circuitry is configured to apply the machine learning model to the cardiac features identified by the feature-based delineation of the sensed ECG data.

11. The device of claim 1, wherein the data comprising the indication that the episode of arrhythmia has occurred in the patient and one or more of the cardiac features that coincide with the episode of arrhythmia comprises at least one of an estimate of the certainty or likelihood that the episode of arrhythmia has occurred in the patient.

12. The device of claim 1, wherein the device comprises a cloud computing device.

13. A system comprising:
an implantable cardiac monitoring device configured to:
sense electrocardiogram (ECG) data of a patient; and
perform feature-based delineation of the sensed ECG data to obtain cardiac features present in the sensed ECG data; and
a computing device configured to:
apply a machine learning model, trained using ECG data for a plurality of patients, to the sensed ECG data of the patient to determine, based on the machine learning model, that an episode of arrhythmia has occurred in the patient;
in response to determining that the episode of arrhythmia has occurred in the patient, generate data comprising an indication that the episode of arrhythmia has occurred in the patient and one or more of the cardiac features that coincide with the episode of arrhythmia.

14. The system of claim 13, wherein, to perform feature-based delineation, the implantable cardiac monitoring device is configured to perform QRS detection.

15. The system of claim 13, wherein the cardiac features present in the sensed ECG data comprise one or more of a mean heartrate of the patient, a minimum heartrate of the patient, a maximum heartrate of the patient, a variability of heartrate of the patient, one or more amplitudes of one or more features of the sensed ECG data of the patient, or an interval between the or more features of the sensed ECG of the patient.

16. The system of claim 13, wherein the computing device is configured to apply the machine learning model to the sensed ECG data of the patient to determine, based on the machine learning model, that that an episode of at least one of bradycardia, tachycardia, or atrial fibrillation has occurred in the patient.

17. The system of claim 13, wherein the computing device is configured to receive, from a user, an adjustment to the feature-based delineation of the cardiac electrogram data in response to the data comprising the indication that the episode of arrhythmia has occurred in the patient and one or more of the cardiac features that coincide with the episode of arrhythmia, and the implantable cardiac monitoring device is configured to perform, in accordance with the adjustment, feature-based delineation of the sensed ECG data to obtain second cardiac features present in the cardiac electrogram data.

18. The system of claim 13, wherein, to generate the data comprising the indication that the episode of arrhythmia has occurred in the patient and one or more of the cardiac features that coincide with the episode of arrhythmia, the computing device is configured to:
identify a subsection of the ECG of the patient, wherein the subsection comprises ECG data for a first time period prior to the episode of arrhythmia, a second time period during the episode of arrhythmia, and a third time period after the episode of arrhythmia, and wherein a length of time of the ECG of the patient is greater than the first, second, and third time periods;
identify one or more of the cardiac features that coincide with the first, second, and third time periods; and
include, in the data, the subsection of the ECG and the one or more of the cardiac features that coincide with the first, second, and third time periods.

19. The system of claim 13, wherein the computing device is configured to:
  process the sensed ECG data to generate an intermediate representation of the sensed ECG data; and
  to apply the machine learning model, apply a machine learning model, trained using intermediate representations of ECG data for a plurality of patients, to the intermediate representation of the sensed ECG data and the cardiac features present in the sensed ECG data to determine, based on the machine learning model, that the episode of arrhythmia has occurred in the patient.

20. The system of claim 13, wherein the implantable cardiac monitoring device is configured to determine a first classification of arrhythmia in the patient based on the feature-based delineation of the sensed ECG data, and the computing device is configured to:
  determine a second classification of arrhythmia based on the application of the machine learning model to the sensed ECG data; and
  determine that the episode of arrhythmia occurred in the patient based on the first classification and second classification.

21. The system of claim 20, wherein, to determine that the episode of arrhythmia has occurred in the patient based on the first classification and second classification, the computing device is configured to:
  determine a degree of similarity of the first classification and the second classification; and
  based on the degree of similarity of the first classification and the second classification, determine that the episode of arrhythmia has occurred in the patient.

22. The system of claim 20, wherein, to determine the first classification of arrhythmia in the patient based on the feature-based delineation of the sensed ECG data the implantable cardiac monitoring device is configured to:
  extract one or more features from the sensed ECG based on the feature-based delineation; and
  apply a model to the one or more extracted features.

23. The system of claim 13, wherein, to apply the machine learning model to the received cardiac electrogram data, the computing device is configured to apply the machine learning model to the cardiac features identified by the feature-based delineation of the received cardiac electrogram data.

24. The system of claim 13, wherein the data comprising the indication that the episode of arrhythmia has occurred in the patient and one or more of the cardiac features that coincide with the episode of arrhythmia comprises at least one of an estimate of the certainty or likelihood that the episode of arrhythmia has occurred in the patient.

25. The system of claim 13, wherein the computing device comprises a cloud computing device.

26. A non-transitory computer-readable storage medium comprising instructions that, when executed by processing circuitry, cause the processing circuitry to:
  apply a machine learning model, trained using electrocardiogram (ECG) data for a plurality of patients, to sensed ECG data of a patient to determine, based on the machine learning model, that an episode of arrhythmia has occurred in the patient;
  perform feature-based delineation of the sensed ECG data to obtain cardiac features present in the sensed ECG data; and
  in response to determining that the episode of arrhythmia has occurred in the patient, generate data comprising an indication that the episode of arrhythmia has occurred in the patient and one or more of the cardiac features that coincide with the episode of arrhythmia.

27. The non-transitory computer-readable storage medium of claim 26, wherein the instructions that cause the processing circuitry to perform feature-based delineation comprise instructions that cause the processing circuitry to perform QRS detection.

28. The non-transitory computer-readable storage medium of claim 26, wherein the cardiac features present in the sensed ECG data comprise one or more of a mean heartrate of the patient, a minimum heartrate of the patient, a maximum heartrate of the patient, a variability of heartrate of the patient, one or more amplitudes of one or more features of the sensed ECG of the patient, or an interval between the or more features of the sensed ECG of the patient.

29. The non-transitory computer-readable storage medium of claim 26, wherein the instructions that cause the processing circuitry to apply the machine learning model to the sensed ECG data of the patient comprise instructions that cause the processing circuitry to determine, based on the machine learning model, that that an episode of at least one of bradycardia, tachycardia, or atrial fibrillation has occurred in the patient.

30. A system comprising:
  processing circuitry configured to:
    apply a machine learning model, trained using ECG data for a plurality of patients, to sensed ECG data of the patient to determine, based on the machine learning model, that an episode of arrhythmia has occurred in the patient; and
    perform feature-based delineation of the sensed ECG data to obtain cardiac features present in the sensed ECG data; and
  means for generating, in response to the determination that the episode of arrhythmia has occurred in the patient, data comprising an indication that the episode of arrhythmia has occurred in the patient and one or more of the cardiac features that coincide with the episode of arrhythmia.

* * * * *